(12) United States Patent
Rosen et al.

(10) Patent No.: US 9,398,960 B2
(45) Date of Patent: Jul. 26, 2016

(54) MULTI-PIECE INTERVERTEBRAL IMPLANTS

(71) Applicant: GLOBUS MEDICAL, INC., Audubon, PA (US)

(72) Inventors: Kyle Rosen, Gilbertsville, PA (US); Jennifer S. Klimek, King of Prussia, PA (US); Daniel Laskowitz, Lancaster, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 14/085,318

(22) Filed: Nov. 20, 2013

(65) Prior Publication Data

US 2014/0121777 A1 May 1, 2014

Related U.S. Application Data

(63) Continuation-in-part of application No. 13/785,856, filed on Mar. 5, 2013, which is a continuation-in-part of application No. 13/559,917, filed on Jul. 27, 2012, now Pat. No. 8,961,606, which is a continuation-in-part of application No. 13/267,119, filed on Oct. 6, 2011.

(60) Provisional application No. 61/535,726, filed on Sep. 16, 2011.

(51) Int. Cl.
  *A61F 2/44* (2006.01)
  *A61F 2/28* (2006.01)
  *A61F 2/30* (2006.01)

(52) U.S. Cl.
  CPC ............ *A61F 2/442* (2013.01); *A61F 2/447* (2013.01); *A61F 2/4455* (2013.01); *A61F 2002/2835* (2013.01); *A61F 2002/3013* (2013.01); *A61F 2002/3039* (2013.01); *A61F 2002/3081* (2013.01); *A61F 2002/30131* (2013.01); *A61F 2002/30332* (2013.01); *A61F 2002/30354* (2013.01); *A61F 2002/30359* (2013.01);

(Continued)

(58) Field of Classification Search
  CPC ....... A61F 2/4455; A61F 2/447; A61F 2/442; A61F 2002/3013; A61F 2002/2835; A61F 2002/30131; A61F 2002/30332; A61F 2002/30354; A61F 2002/30359; A61F 2002/30383; A61F 2002/30385; A61F 2002/3039; A61F 2002/30405; A61F 2002/30418; A61F 2003/30433; A61F 2002/30448; A61F 2002/30472; A61F 2002/30487; A61F 2002/30492; A61F 2002/30599; A61F 2002/30604; A61F 2002/30607; A61F 2002/30772; A61F 2002/30785; A61F 2002/30787; A61F 2002/30808; A61F 2002/3081; A61F 2002/30822; A61F 2002/30828; A61F 2002/30836; A61F 2002/30841; A61F 2002/30843; A61F 2002/30904; A61F 2002/4475; A61F 2310/00359; A61F 2310/00017; A61F 2310/00023
  USPC ............ 623/17.11–17.16, 23.5, 23.51, 23.61, 623/23.63
  See application file for complete search history.

(56) References Cited

U.S. PATENT DOCUMENTS

| | | |
|---|---|---|
| 5,609,635 A | 3/1997 | Michelson |
| 5,728,159 A | 3/1998 | Stroever |

(Continued)

*Primary Examiner* — Pedro Philogene

(57) ABSTRACT

Intervertebral implants for implanting into an intervertebral space are provided. The implants can comprise one or more layers that are operably attached to one another. An implant can comprise a first layer having a first mating surface that mates with a second mating surface of a second layer. The first mating surface and the second mating surface can have features that allow them to complement each other. The implants can include one or more bore holes for receiving a fixation member. The bore holes can be horizontal, vertical or diagonal. In some cases, the bore holes will be blind bore holes.

18 Claims, 51 Drawing Sheets

(52) U.S. Cl.
CPC ............... *A61F2002/30383* (2013.01); *A61F 2002/30385* (2013.01); *A61F 2002/30387* (2013.01); *A61F 2002/30405* (2013.01); *A61F 2002/30418* (2013.01); *A61F 2002/30433* (2013.01); *A61F 2002/30448* (2013.01); *A61F 2002/30472* (2013.01); *A61F 2002/30487* (2013.01); *A61F 2002/30492* (2013.01); *A61F 2002/30599* (2013.01); *A61F 2002/30604* (2013.01); *A61F 2002/30607* (2013.01); *A61F 2002/30772* (2013.01); *A61F 2002/30785* (2013.01); *A61F 2002/30787* (2013.01); *A61F 2002/30808* (2013.01); *A61F 2002/30822* (2013.01); *A61F 2002/30828* (2013.01); *A61F 2002/30836* (2013.01); *A61F 2002/30841* (2013.01); *A61F 2002/30843* (2013.01); *A61F 2002/30904* (2013.01); *A61F 2002/4475* (2013.01); *A61F 2310/00017* (2013.01); *A61F 2310/00023* (2013.01); *A61F 2310/00359* (2013.01)

(56) References Cited

U.S. PATENT DOCUMENTS

| | | | |
|---|---|---|---|
| 5,741,253 | A | 4/1998 | Michelson |
| 5,814,084 | A | 9/1998 | Grivas |
| 5,888,227 | A | 3/1999 | Cottle |
| 5,899,939 | A | 5/1999 | Boyce |
| 5,972,368 | A | 10/1999 | Mckay |
| 5,989,289 | A | 11/1999 | Coates |
| 6,025,538 | A | 2/2000 | Yaccarino, III |
| 6,033,438 | A | 3/2000 | Bianchi |
| 6,096,081 | A | 8/2000 | Grivas |
| 6,143,033 | A | 11/2000 | Paul |
| 6,174,311 | B1 | 1/2001 | Branch |
| 6,200,347 | B1 | 3/2001 | Anderson et al. |
| 6,206,923 | B1 | 3/2001 | Boyd |
| 6,235,059 | B1 | 5/2001 | Benezech et al. |
| 6,245,108 | B1 | 6/2001 | Biscup |
| 6,258,125 | B1 | 7/2001 | Paul et al. |
| 6,261,586 | B1 | 7/2001 | Mckay |
| 6,270,528 | B1 | 8/2001 | Mckay |
| 6,294,187 | B1 | 9/2001 | Boyce |
| 6,296,664 | B1 | 10/2001 | Middleton |
| 6,350,283 | B1 | 2/2002 | Michelson |
| 6,371,988 | B1 | 4/2002 | Pafford |
| 6,379,385 | B1 | 4/2002 | Kalas |
| 6,398,811 | B1 | 6/2002 | Mckay |
| 6,409,765 | B1 | 6/2002 | Bianchi |
| 6,432,436 | B1 | 8/2002 | Gertzman |
| 6,458,158 | B1 | 10/2002 | Anderson et al. |
| 6,468,311 | B2 * | 10/2002 | Boyd ............... A61F 2/28 623/17.11 |
| 6,482,233 | B1 | 11/2002 | Aebi |
| 6,511,509 | B1 | 1/2003 | Ford |
| 6,520,993 | B2 | 2/2003 | James |
| 6,548,080 | B1 | 4/2003 | Gertzman |
| 6,554,863 | B2 | 4/2003 | Paul |
| 6,579,318 | B2 | 6/2003 | Varga |
| 6,610,065 | B1 | 8/2003 | Branch |
| 6,632,247 | B2 | 10/2003 | Boyer, II |
| 6,638,310 | B2 | 10/2003 | Lin |
| 6,652,593 | B2 | 11/2003 | Boyer, II |
| 6,660,038 | B2 | 12/2003 | Boyer, II |
| 6,666,890 | B2 | 12/2003 | Michelson |
| 6,676,703 | B2 | 1/2004 | Biscup |
| 6,695,882 | B2 | 2/2004 | Bianchi |
| 6,706,067 | B2 | 3/2004 | Shimp |
| 6,719,794 | B2 | 4/2004 | Gerber |
| 6,761,738 | B1 | 7/2004 | Boyd |
| 6,761,739 | B2 | 7/2004 | Shepard |
| 6,764,491 | B2 | 7/2004 | Frey |
| 6,767,369 | B2 | 7/2004 | Boyer, II |
| 6,776,800 | B2 | 8/2004 | Boyer, II |
| RE38,614 | E | 10/2004 | Paul |
| 6,808,585 | B2 | 10/2004 | Boyce |
| 6,830,570 | B1 | 12/2004 | Frey |
| 6,852,126 | B2 | 2/2005 | Ahlgren |
| 6,855,167 | B2 * | 2/2005 | Shimp ............... A61F 2/28 403/408.1 |
| 6,855,169 | B2 | 2/2005 | Boyer, II |
| 6,902,578 | B1 | 6/2005 | Anderson et al. |
| 6,929,662 | B1 | 8/2005 | Messerli |
| 6,974,480 | B2 | 12/2005 | Messerli |
| 6,986,788 | B2 | 1/2006 | Paul |
| 7,014,659 | B2 | 3/2006 | Boyer, II |
| 7,018,412 | B2 | 3/2006 | Ferreira |
| 7,018,413 | B2 | 3/2006 | Krüger |
| 7,022,137 | B2 | 4/2006 | Michelson |
| 7,044,968 | B1 | 5/2006 | Yaccarino et al. |
| 7,048,762 | B1 | 5/2006 | Sander |
| 7,048,765 | B1 | 5/2006 | Grooms |
| 7,060,073 | B2 | 6/2006 | Frey |
| 7,060,096 | B1 | 6/2006 | Schopf |
| 7,087,082 | B2 | 8/2006 | Paul |
| 7,087,087 | B2 | 8/2006 | Boyer, II |
| 7,115,146 | B2 | 10/2006 | Boyer, II |
| 7,137,997 | B2 | 11/2006 | Paul |
| 7,192,447 | B2 | 3/2007 | Rhoda |
| 7,223,292 | B2 | 5/2007 | Messerli |
| 7,226,482 | B2 | 6/2007 | Messerli |
| 7,226,483 | B2 | 6/2007 | Gerber |
| 7,229,477 | B2 | 6/2007 | Biscup |
| 7,300,465 | B2 | 11/2007 | Paul |
| 7,309,357 | B2 | 12/2007 | Kim |
| 7,309,359 | B2 | 12/2007 | Trieu |
| 7,323,011 | B2 | 1/2008 | Shepard et al. |
| 7,347,873 | B2 | 3/2008 | Paul |
| 7,435,262 | B2 | 10/2008 | Michelson |
| 7,473,277 | B2 | 1/2009 | Boyer, II |
| 7,479,160 | B2 | 1/2009 | Branch |
| 7,481,812 | B2 | 1/2009 | Frey |
| 7,491,237 | B2 | 2/2009 | Randall |
| 7,601,173 | B2 | 10/2009 | Messerli |
| 7,618,460 | B2 | 11/2009 | Boyd |
| 7,637,953 | B2 | 12/2009 | Branch |
| 7,662,184 | B2 | 2/2010 | Edwards |
| 7,662,185 | B2 | 2/2010 | Alfaro |
| 7,726,002 | B2 | 6/2010 | Shimp |
| 7,753,963 | B2 | 7/2010 | Boyer, II |
| 7,815,682 | B1 | 10/2010 | Peterson |
| 7,833,271 | B2 | 11/2010 | Mitchell |
| 7,846,207 | B2 | 12/2010 | Lechmann et al. |
| 7,862,616 | B2 | 1/2011 | Lechmann et al. |
| 7,879,103 | B2 | 2/2011 | Gertzman |
| 7,918,888 | B2 | 4/2011 | Hamada |
| 7,918,891 | B1 | 4/2011 | Curran et al. |
| 7,931,692 | B2 | 4/2011 | Sybert |
| 7,938,857 | B2 | 5/2011 | Garcia-bengochea |
| 7,967,867 | B2 | 6/2011 | Barreiro |
| 8,273,127 | B2 | 9/2012 | Jones et al. |
| 8,328,872 | B2 | 12/2012 | Duffield et al. |
| 8,685,099 | B2 * | 4/2014 | Bhattacharya ........ A61F 2/4455 623/17.11 |
| 2001/0010021 | A1 | 7/2001 | Boyd |
| 2002/0106393 | A1 | 8/2002 | Bianchi |
| 2002/0120334 | A1 | 8/2002 | Crozet |
| 2002/0138143 | A1 | 9/2002 | Grooms |
| 2003/0135275 | A1 * | 7/2003 | Garcia et al. ............... 623/17.11 |
| 2004/0054412 | A1 | 3/2004 | Gerbec et al. |
| 2004/0172133 | A1 | 9/2004 | Gerber |
| 2005/0261771 | A1 | 11/2005 | Paul et al. |
| 2006/0142828 | A1 | 6/2006 | Schorr |
| 2006/0241760 | A1 | 10/2006 | Randall |
| 2007/0255414 | A1 | 11/2007 | Melkent |
| 2007/0270957 | A1 | 11/2007 | Heinz |
| 2007/0270965 | A1 * | 11/2007 | Ferguson ............... 623/17.11 |
| 2008/0046090 | A1 | 2/2008 | Paul |
| 2008/0125865 | A1 | 5/2008 | Abdelgany |
| 2008/0154379 | A1 | 6/2008 | Steiner |
| 2008/0161919 | A1 | 7/2008 | Melkent |
| 2008/0188940 | A1 | 8/2008 | Cohen |
| 2008/0188945 | A1 * | 8/2008 | Boyce et al. ............... 623/23.61 |

(56) References Cited

U.S. PATENT DOCUMENTS

| | | |
|---|---|---|
| 2008/0249622 A1 | 10/2008 | Gray |
| 2009/0099661 A1 | 4/2009 | Bhattacharya |
| 2009/0101582 A1 | 4/2009 | Liu |
| 2010/0204739 A1 | 8/2010 | Bae et al. |
| 2011/0160864 A1 | 6/2011 | Messerli |
| 2012/0101580 A1 | 4/2012 | Lechmann et al. |
| 2012/0130495 A1 | 5/2012 | Duffield et al. |
| 2012/0130496 A1 | 5/2012 | Duffield et al. |
| 2012/0179259 A1 | 7/2012 | Mcdonough et al. |
| 2012/0226357 A1* | 9/2012 | Varela .................. 623/17.16 |
| 2012/0323330 A1 | 12/2012 | Kueenzi et al. |

* cited by examiner

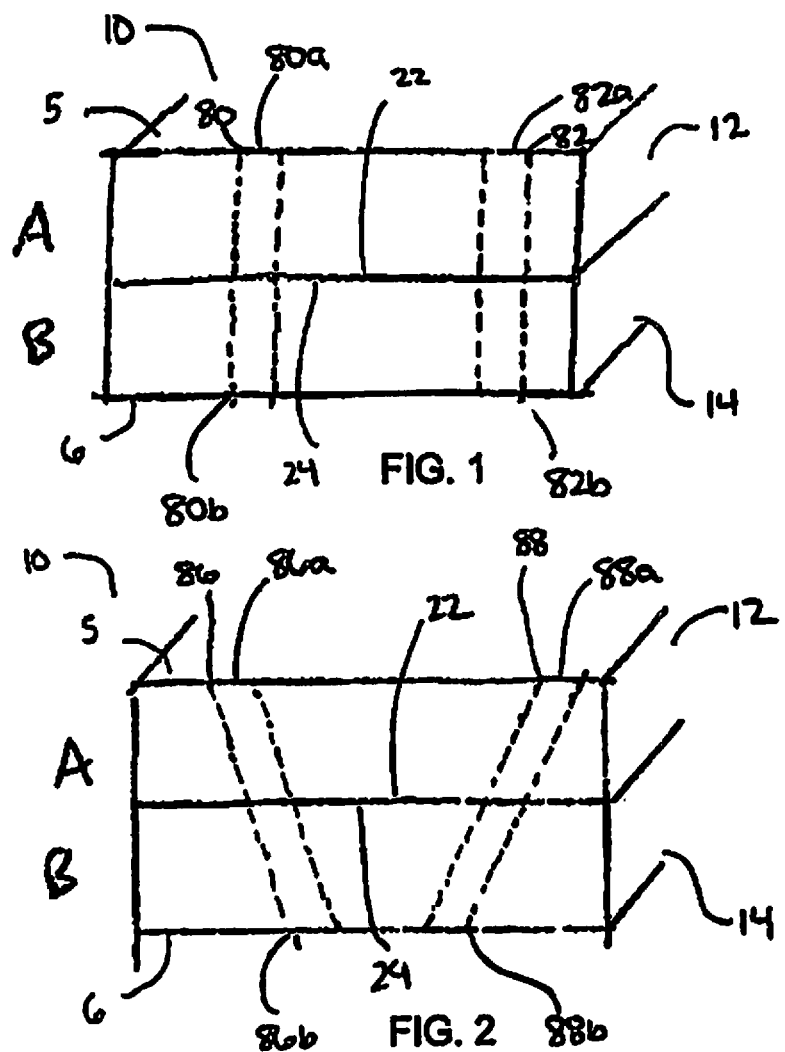
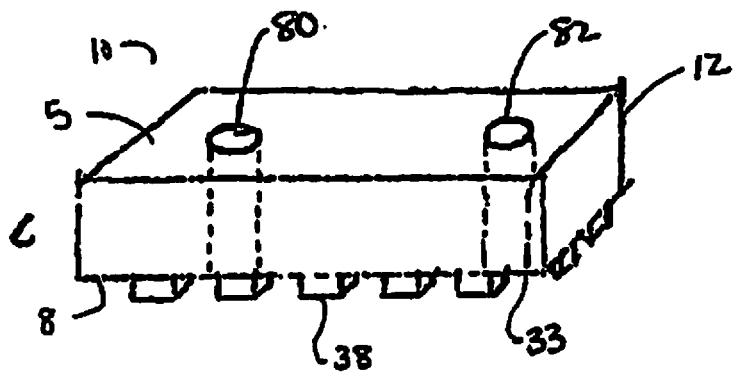
FIG. 1
FIG. 2
FIG. 3

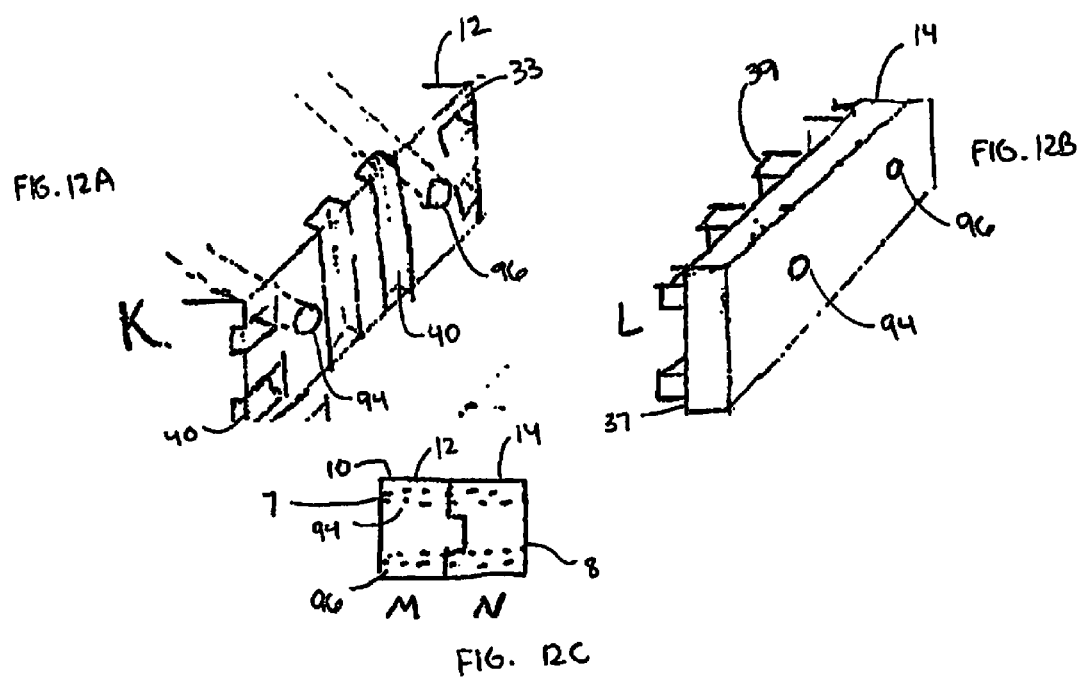

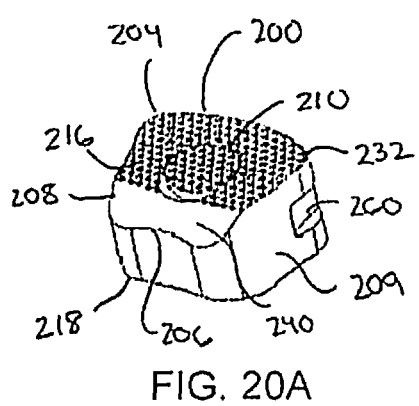
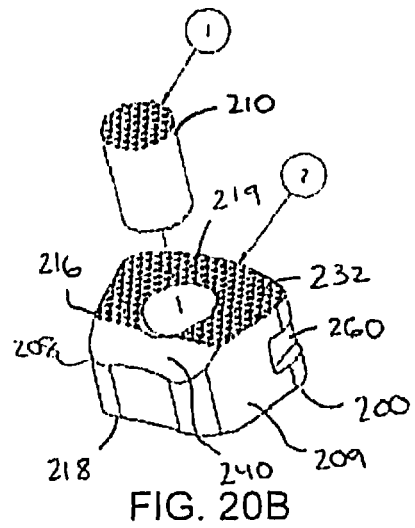
FIG. 20A    FIG. 20B
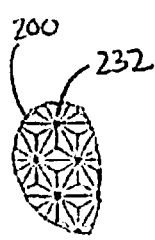
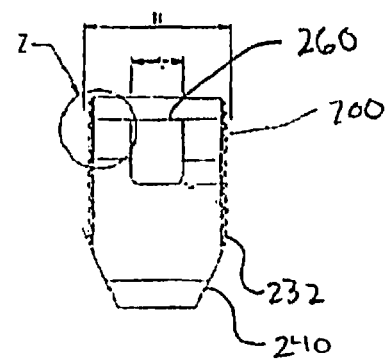
FIG. 20C    FIG. 20D

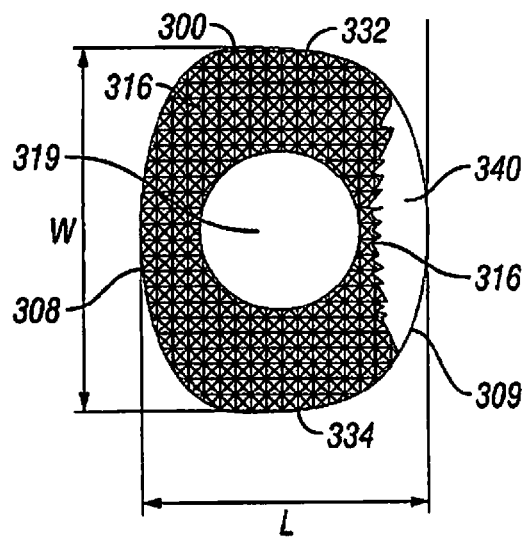
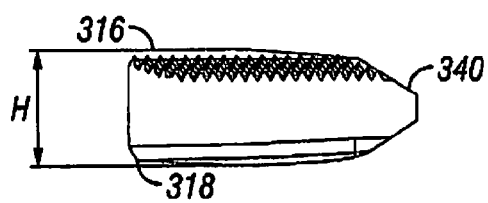
FIG. 21A
FIG. 21B
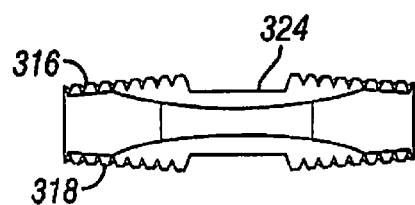
FIG. 21C
FIG. 21D

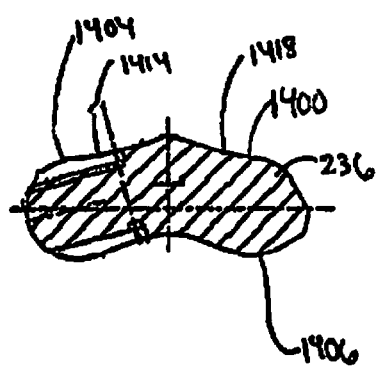
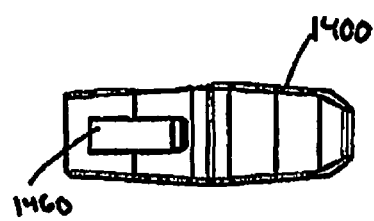
FIG. 28A                FIG. 28B
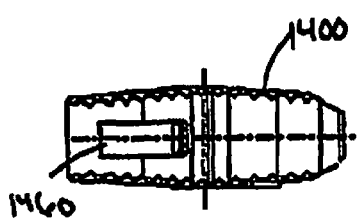
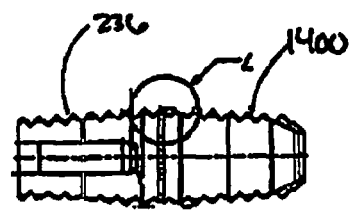
FIG. 28C                FIG. 28D
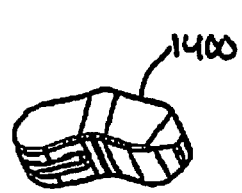
FIG. 28E

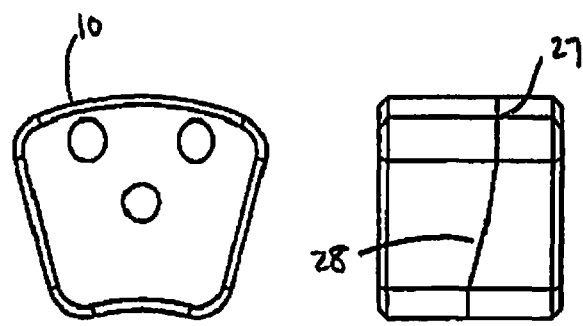
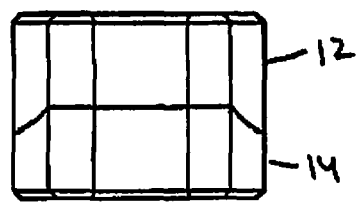
FIG. 34A
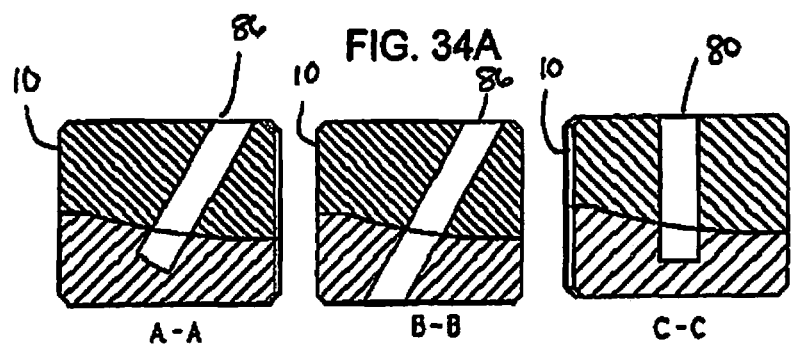
FIG. 34B
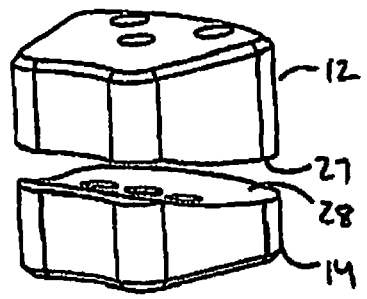
FIG. 34C

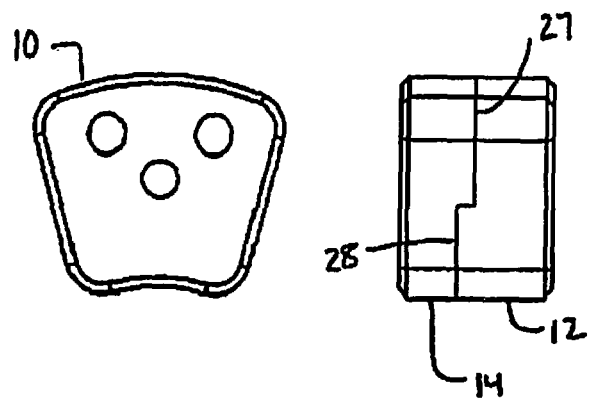
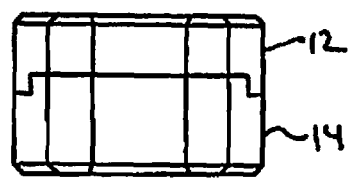
FIG. 35A
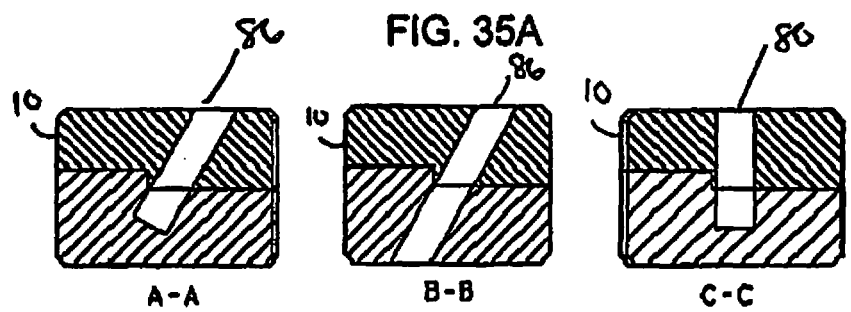
FIG. 35B
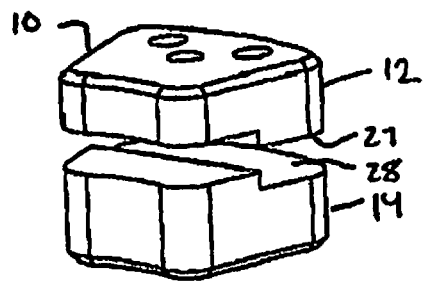
FIG. 35C

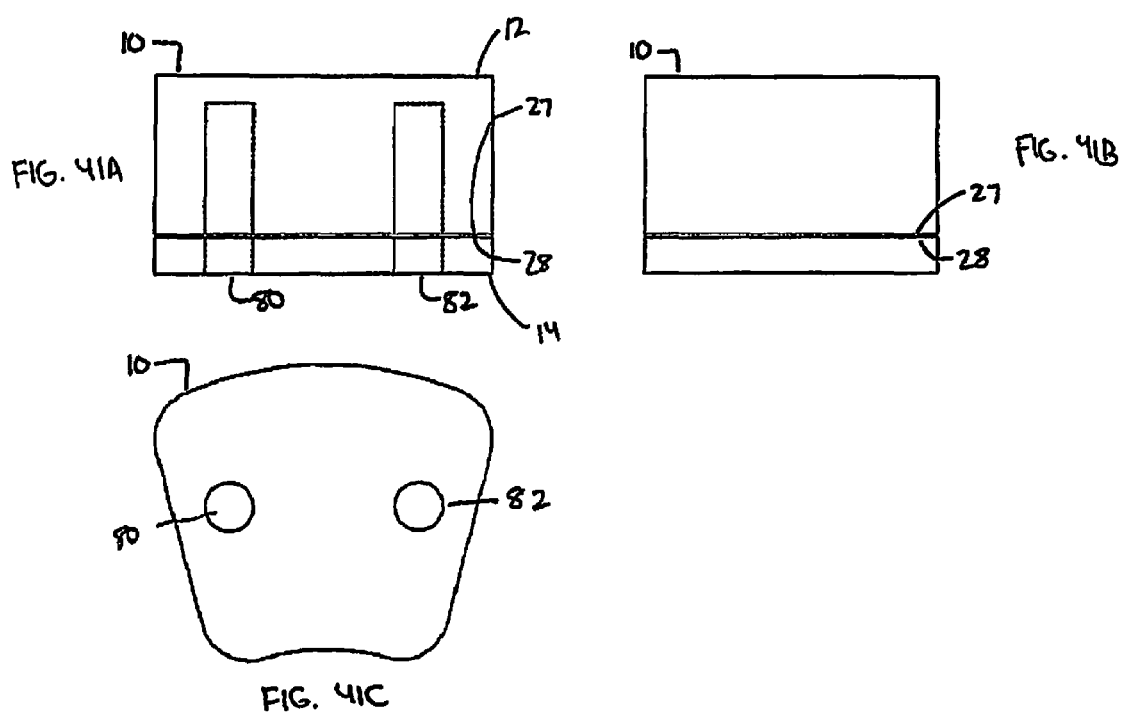

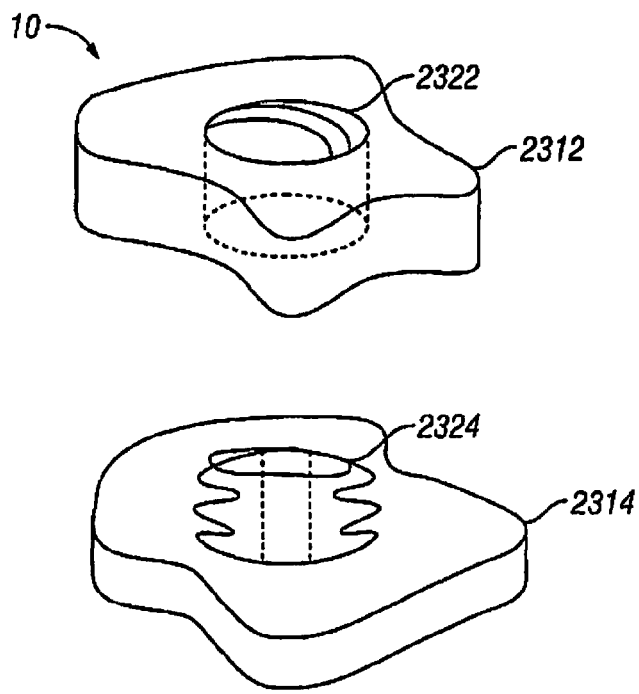
FIG. 51
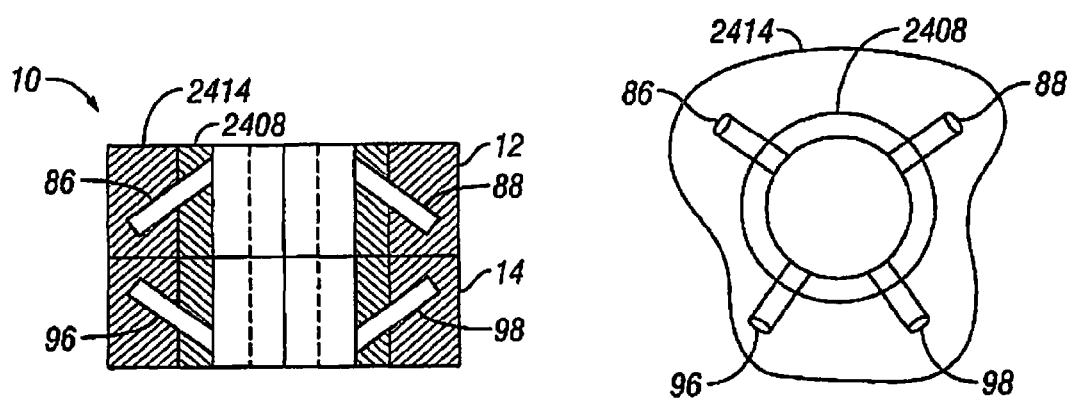
FIG. 52A
FIG. 52B

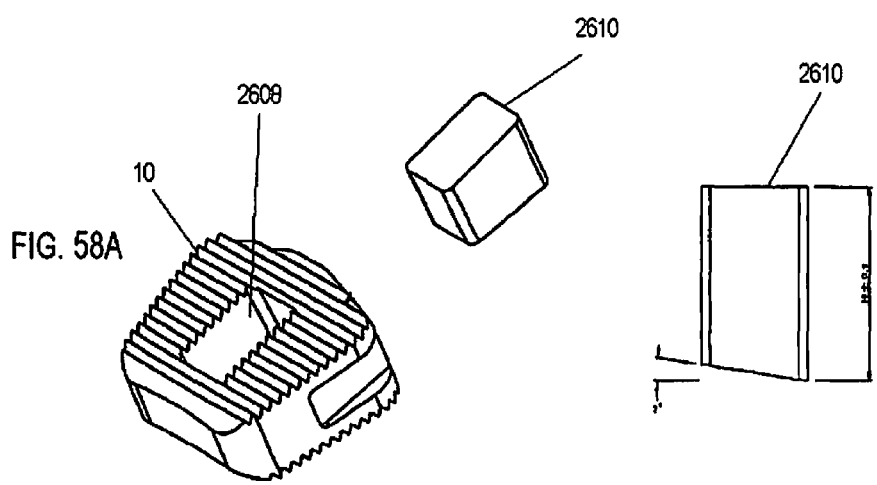
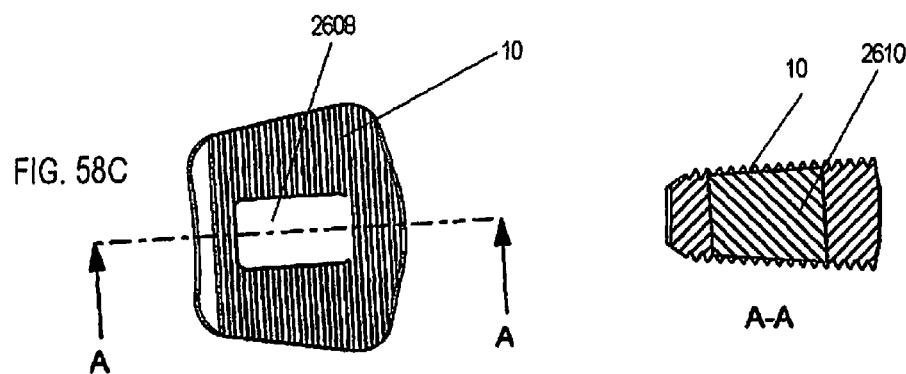

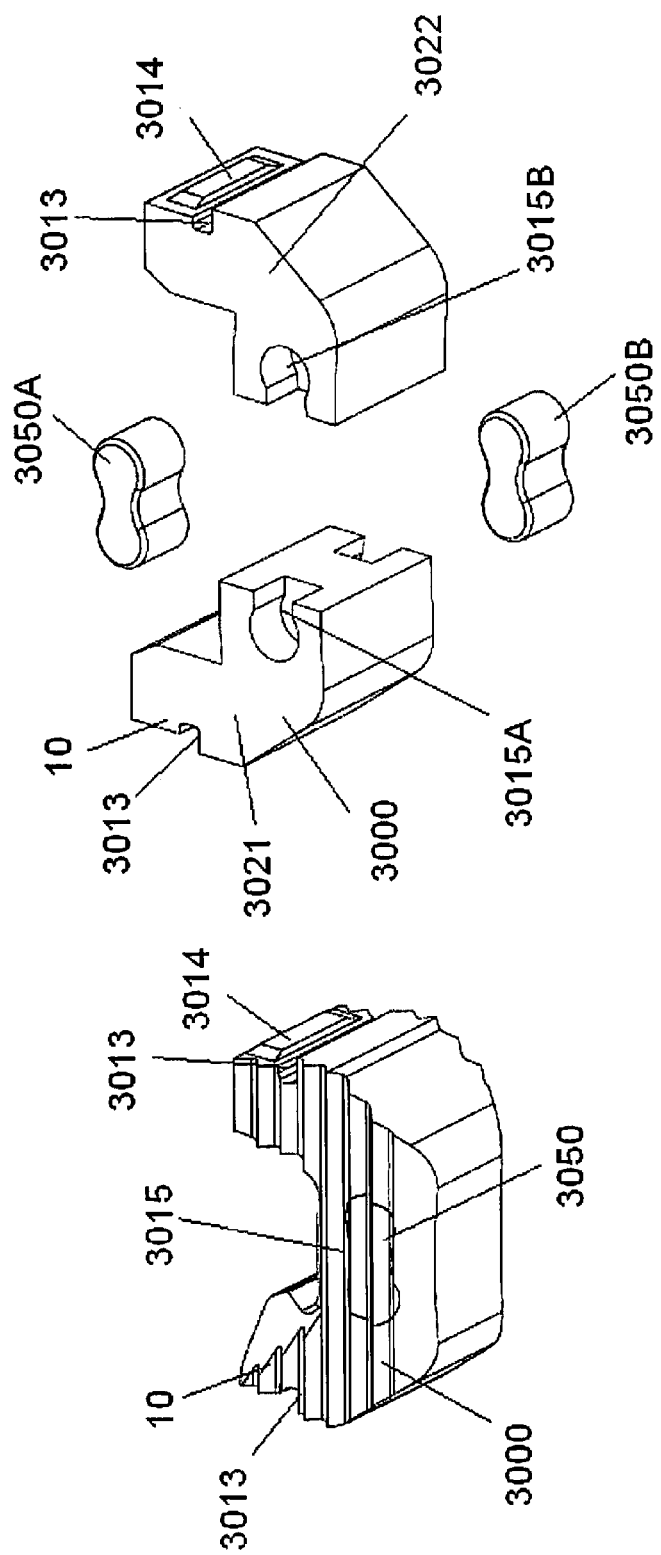

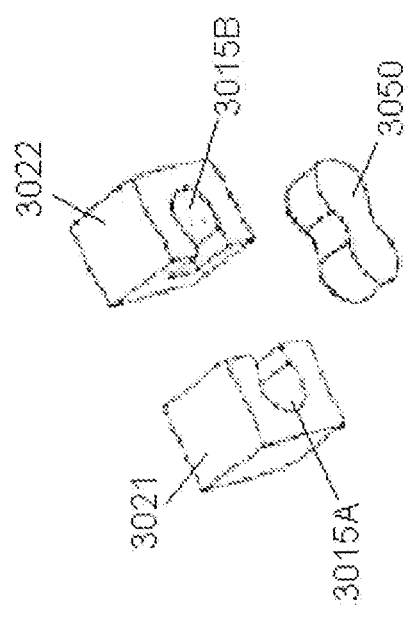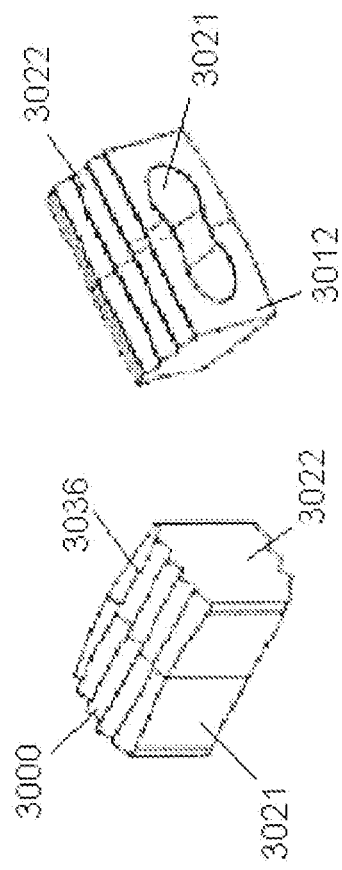

MULTI-PIECE INTERVERTEBRAL IMPLANTS

CROSS REFERENCE TO RELATED APPLICATIONS

This patent application is a continuation-in-part application of U.S. patent application Ser. No. 13/785,856, filed Mar. 5, 2013, which is a continuation-in-part of U.S. patent application Ser. No. 13/559,917, filed Jul. 27, 2012, which is a continuation-in-part of Ser. No. 13/267,119, filed Oct. 6, 2011, which claims priority to U.S. Provisional Application 61/535,726, filed on Sep. 16, 2011, the entire contents of which are incorporated by reference.

FIELD OF THE INVENTION

The present invention is generally directed to intervertebral implants and in particular, spacers for introducing into an intervertebral space.

BACKGROUND OF THE INVENTION

Spinal fusion procedures are performed to alleviate pain caused by trauma, disc herniation or spondylosis. In some procedures, portions of a spinal disc can be removed and replaced by an intervertebral implant designed to assist in the fusion process. There thus is a need for improved intervertebral implants that can be inserted into an intervertebral space between two vertebrae.

SUMMARY OF THE INVENTION

Various embodiments of intervertebral implants are provided. In some embodiments, an intervertebral implant comprises a first layer having a superior surface for contacting a vertebral body and a second layer having an inferior surface for contacting a vertebral body. The second layer is operably attached to the first layer. The implant further comprises a bore hole that extends through at least a portion of the first layer and the second layer, wherein the bore hole has a first opening that opens at one of either the superior surface of the first layer or the inferior surface of the second layer and a second opening that is blocked by one of either the first layer or the second layer.

In other embodiments, an intervertebral implant comprises a first layer having a superior surface for contacting a vertebral body and a second layer having an inferior surface for contacting a vertebral body. The second layer is operably attached to the first layer to form a single-bodied implant. The implant further comprises a bore hole that extends through at least a portion of the first layer and the second layer, wherein the bore hole has a first opening that opens at one of either the superior surface of the first layer or the inferior surface of the second layer and a second opening that opens at a sidewall of the single-bodied implant formed by the first layer and the second layer.

In other embodiments, an intervertebral implant comprises a first layer having a first upper surface for contacting a vertebral body and a first lower surface opposite the first upper surface. The first lower surface includes one or more stepped features. The implant further comprises a second layer having a second lower surface for contacting a vertebral body and a second lower surface opposite the second upper surface. The second upper surface includes one or more stepped features that complement the first lower surface of the first layer when the first layer and second layer are pressed together. In addition, the implant comprises a bore hole that extends through at least a portion of the first layer and the second layer.

BRIEF DESCRIPTION OF THE DRAWINGS

The invention will be more readily understood with reference to the embodiments thereof illustrated in the attached figures, in which:

FIG. 1 is a front perspective view of a multi-layered implant having flat faces and vertical bore holes formed therein according to some embodiments.

FIG. 2 is front perspective view of a multi-layered implant having flat faces and diagonal bore holes formed therein according to some embodiments.

FIG. 3 is a top perspective view of a layer of a multi-layered implant having a face with a waffle pattern according to some embodiments.

FIGS. 12A-12C illustrate different views of a multi-layered implant including horizontal bore holes according to some embodiments.

FIGS. 20A-20D illustrate different views of an implant having teeth according to some embodiments.

FIGS. 21A-21D illustrate different views of an alternative implant having teeth according to some embodiments.

FIGS. 28A-28E illustrate different views of an alternative implant having ridges according to some embodiments.

FIGS. 34A-34C illustrate different views of an alternative multi-layered implant having various mating features according to some embodiments.

FIGS. 35A-35C illustrate different views of an alternative multi-layered implant having various mating features according to some embodiments.

FIGS. 41A-41C illustrate some embodiments of an alternative multi-piece implant having a pair of bore holes.

FIG. 51 illustrates a multi-piece implant having threaded components according to some embodiments.

FIGS. 52A and 52B illustrate a multi-piece implant having a concentric inner member according to some embodiments.

FIGS. 58A-58D illustrate an alternative implant for receiving a plug according to some embodiments.

FIGS. 62A and 62B illustrate different views of an alternative implant with a figure 8 pin according to some embodiments.

FIG. 63 illustrates an unassembled implant with a figure 8 pin according to some embodiments.

FIGS. 64A and 64B illustrate different views of an assembled implant with a figure 8 pin according to some embodiments.

DETAILED DESCRIPTION OF THE ILLUSTRATED EMBODIMENTS

Figure 4:
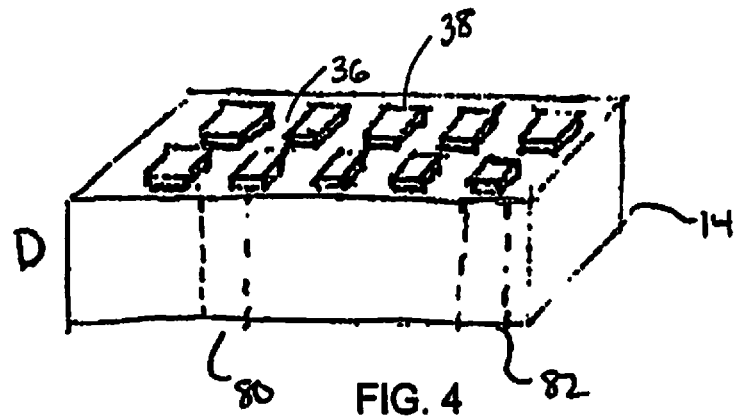
FIG. 4 is a top perspective view of a complementary layer to the layer in FIG. 3 according to some embodiments.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present application describes intervertebral implants that are configured to be implanted in an intervertebral space between two vertebrae. The implants can comprise one or more spacers, cages, wedges, rings, etc. that are insertable into a disc space. The implants can remain in the intervertebral space for an extended period of time and can assist in interbody fusion processes.

In some embodiments, the intervertebral implants comprise single-piece or multi-piece spacers. The multi-piece spacers can include two, three, four or more layers that are placed horizontally, vertically, or in any orientation relative to one another. The spacers can be formed of a number of different types of materials, including various metals such as titanium and stainless steel, metallic alloys, polymers such as PEEK and combinations thereof. In other embodiments, the spacers are formed of a bone-material, either natural or synthetic. In some embodiments, the bone-material can include allograft bone, autograft bone, xenograft bone or combinations thereof. The material for such allograft spacers can be taken, for example, from a diaphysis of a long bone.

FIGS. 1-19 illustrate various embodiments of multi-piece spacers having layers with multiple features according to some embodiments. While the different layers of material can be held together using an adhesive, in most of the illustrated embodiments, a fixation device, such as a screw, pin or interference fit device is used to secure the layers together. In some embodiments, the fixation device can be inserted into a bore hole formed through one or more layers of the implant.

FIG. 1 illustrates a multi-piece implant 10 comprised of two layers 12, 14 of material. Each of the layers 12, 14 has a mating face 22, 24. Both mating face 22 and 24 are illustrated as flat. When the two layers 12, 14 are pressed and secured together, they form an intervertebral implant that can be inserted into a vertebral space. In some embodiments, additional layers can be attached to layers 12, 14, thereby forming an implant with more than two layers. The advantage of having multi-piece implants is that the implants can be sized accurately using more or less layers to fit within an intervertebral space along different levels of the spine for patients of different sizes.

Each of the layers 12, 14 has two vertical bore holes 80, 82 formed therein. Layer 12 has vertical bore holes 80a, 82a, while layer 14 has vertical bore holes 80b, 82b. The vertical bore holes 80a, 82a in layer 12 correspond with and align with the vertical bore holes 80b, 82b in the other layer 14, thereby forming the two continuous bore holes 80, 82 through the implant. The bore holes 80, 82 are configured to receive a fixation device, such as a pin or screw, to secure the first layer 12 to the second layer 14. For purposes of this application, the term "bore hole" can refer to a bore hole through a single layer, or a continuous bore hole formed by multiple bore holes formed through multiple layers.

The bore holes 80, 82 in FIG. 1 extend from a superior face 5 (e.g., the top surface of representative layer A) to an inferior face 6 (e.g., the bottom surface of representative layer B). Each of these faces 5, 6 are configured to contact a vertebral body, such as an adjacent superior and inferior vertebral body. In other embodiments, the bore holes 80, 82 need not extend all the way through a superior face 5 and an inferior face 6. For example, the bore holes can be blind bore holes, in which at least one side of the bore hole is blocked or enclosed, as shown in FIG. 32B. In other words, for a blind bore hole, at least one of the openings is covered or enclosed. Alternatively, the bore holes can extend from a top or bottom surface into a side surface, such they will not extend completely through from a superior face to an inferior face, as shown in FIG. 42.

FIG. 2 also illustrates a multi-piece implant 10 comprised of two layers 12, 14, of material. While the multi-piece implant 10 has flat faces, as in the previously described implant, the implant 10 in FIG. 2 includes two diagonal bore holes 86, 88 instead of two vertical bore holes. The two diagonal bore holes 86, 88 are formed from bore holes 86a, 88a in layer 12 that extend continuously with the bore holes 86b, 88b in layer 14. As shown in FIG. 2, the bore holes 86, 88 extend through the implant from a superior face 5 to an inferior face 6. In other embodiments, the bore holes can extend through an implant from a posterior face to an anterior face, or through an implant from a first sidewall to a second sidewall.

FIG. 3 illustrates a single layer 12 of a multi-piece implant 10 having vertical bore holes 80, 82 and a mating face 8 comprising a waffle-pattern. The vertical bore holes 80, 82 are configured to receive a fixation device for securing the layer to a second layer 14, shown in FIG. 4.

As shown in FIG. 3, the layer 12 can include a mating face 33 that includes a plurality of square or rectangular protrusions 38. The protrusions 38 form a waffle-pattern on the face 33 that is capable of mating with a complementary face 36 of another layer 14, as shown in FIG. 4. In other embodiments, the protrusions 38 are not square or rectangular, but are of various other shapes, such as tear-shaped or trapezoidal.

FIG. 4 illustrates a layer 14 that is complementary to the layer 12. The layer 14 includes a complementary face 36 that also includes square or rectangular protrusions 38. The protrusions 38 in the first layer 12 fit into the voids formed between the protrusions 38 in the second layer 12, thereby forming an interlocking implant. In other words, the waffle pattern on the mating face 36 of layer D is configured to fit and complement the waffle pattern on the mating face 33 of layer C, thereby forming a two layer spacer that can be inserted into an intervertebral space. As shown in FIGS. 3 and 4, vertical pin holes 80, 82 can extend through the implant 10.

The waffle pattern on the layer can mate with one or more complementary patterns on other layers, such that two layers can be conveniently mated. As shown in FIG. 3, the waffle pattern is formed of square and/or rectangular formations that have edges. However, in other embodiments, the waffle pattern can be formed by other formations of different geometrical shapes, such as triangular protrusions.

Figure 5:
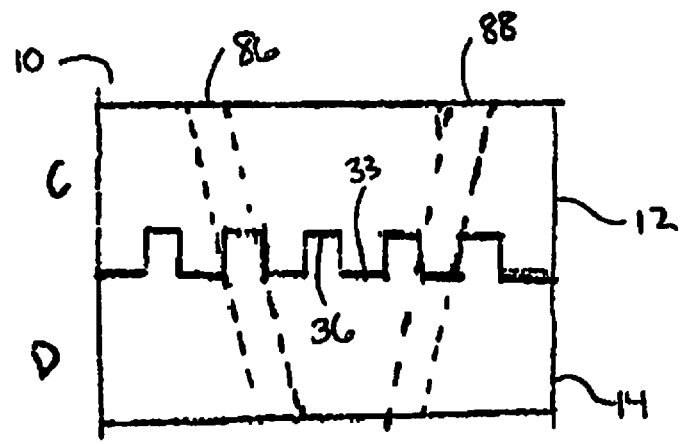
FIG. 5 is a cross-sectional view of a multi-layered implant having layers with mated waffle faces according to some embodiments.

FIG. 5 is a cross-sectional view of a multi-layered implant 10 having layers 12, 14 with mated waffle faces according to some embodiments. Layer 12 includes a mating face 33 with square or rectangular protrusions that complements the mating face 33 of layer 14. As shown in FIG. 5, the multi-layered implant 10 includes diagonal bore holes 86, 88 for receiving one or more fixation devices.

Figure 6:
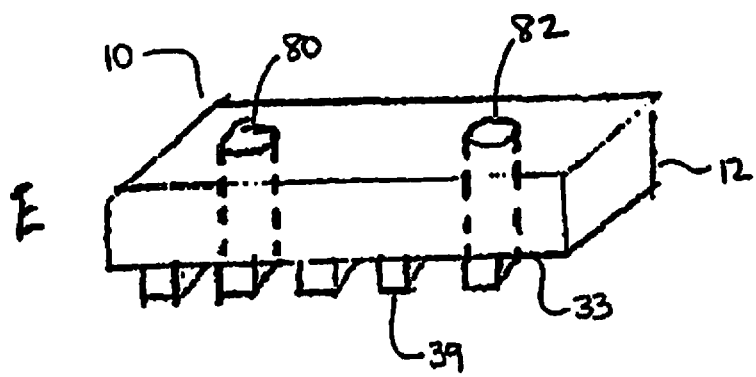
FIG. 6 is a top perspective view of a layer of a multi-layered implant having block features according to some embodiments.

FIG. 6 illustrates a layer 12 of a multi-piece implant 10 having two vertical bore holes 80, 82. The layer in FIG. 6 includes a mating face 33 having protruding features comprising multiple block features 39 in parallel to one another. Advantageously, the blocks 39 extend from one side of the implant to another, thereby forming a mating surface that is continuous throughout a length of the side of the implant. While the blocks 39 are illustrated as being of similar size and evenly distributed, in other embodiments, the blocks 39 can be of different size and or distributed unevenly along the length of the spacer.

Figure 7:
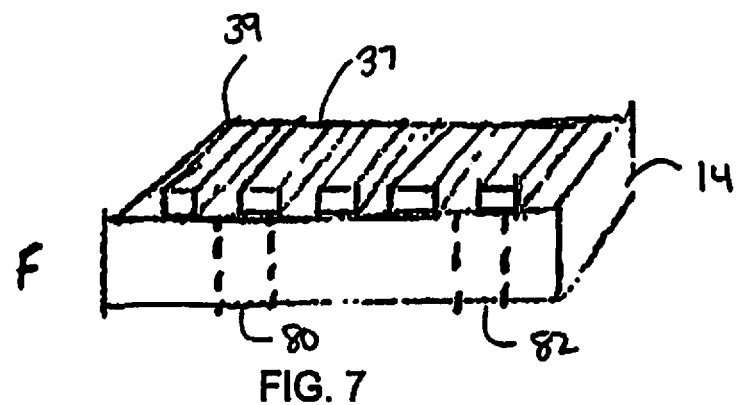
FIG. 7 is a top perspective view of a complementary layer to the layer in FIG. 6 according to some embodiments.

FIG. 7 illustrates a layer 14 of a multi-piece implant designed to correspond and mate with the layer 12 in FIG. 6. The representative layer F in FIG. 7 includes a mating face 37 having multiple block features 39 in parallel that is designed to interlock with the layer in FIG. 6. The layer in FIG. 7 also includes two vertical bore holes that are designed to match with the vertical bore holes in FIG. 6 to form two continuous bore holes that extend through implant 10.

Figure 8:
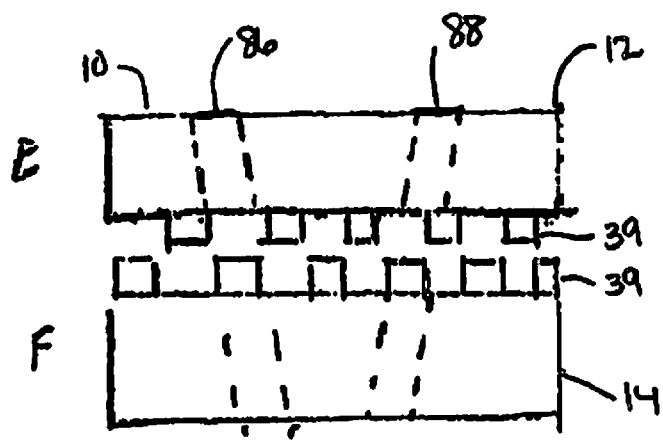
FIG. 8 is a cross-sectional view of a multi-layered implant having block features and diagonal bore holes formed therein according to some embodiments.

FIG. 8 illustrates a cross-sectional view of a multi-piece implant 10 formed of two layers 12, 14. Each of the layers 12, 14 has a face including a plurality of block features 39, as shown in FIGS. 6 and 7. The two layers 12, 14 include a pair of diagonal bore holes 86, 88 that extend through the implant.

Figure 9A:
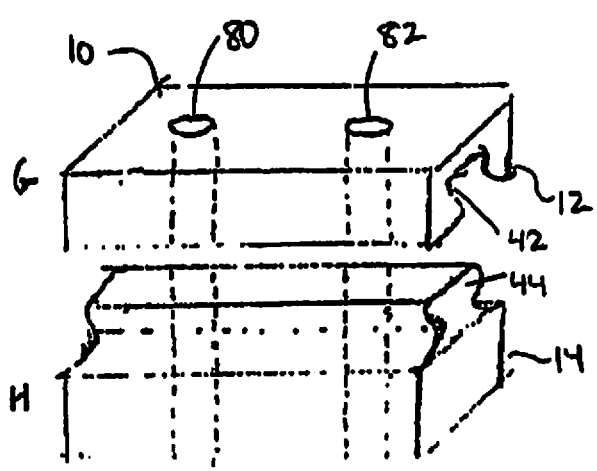
FIGS. 9A and 9B illustrate different views of a multi-layered implant having layers with interlocking curved faces according to some embodiments.
Figure 9B:
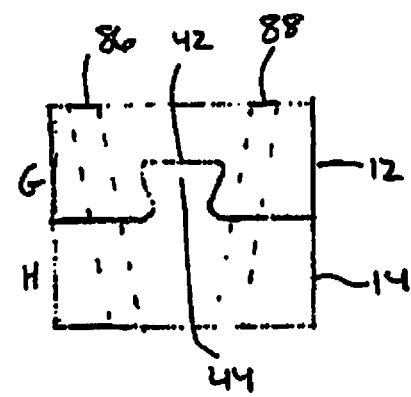

FIGS. 9A and 9B illustrate different views of a multi-piece implant 10 formed of two interlocking layers 12, 14 according to some embodiments. Layer 12 includes a shaped "dovetail" groove 42 designed to receive a complementary mating feature 44 protruding from a surface of layer 14. Advantageously, the mating feature 44 is curved, which helps to securely interlock layer 14 into layer 12, thereby forming a secure implant.

As shown in the figures, a pair of bore holes can be formed through the implant 10. The bore holes can be vertical bore holes 80, 82, as in FIG. 9A, or diagonal bore holes 86, 88, as in FIG. 9B. In other embodiments, combinations of vertical and diagonal bore holes are also possible.

Figures 10A, 10B, 10C:
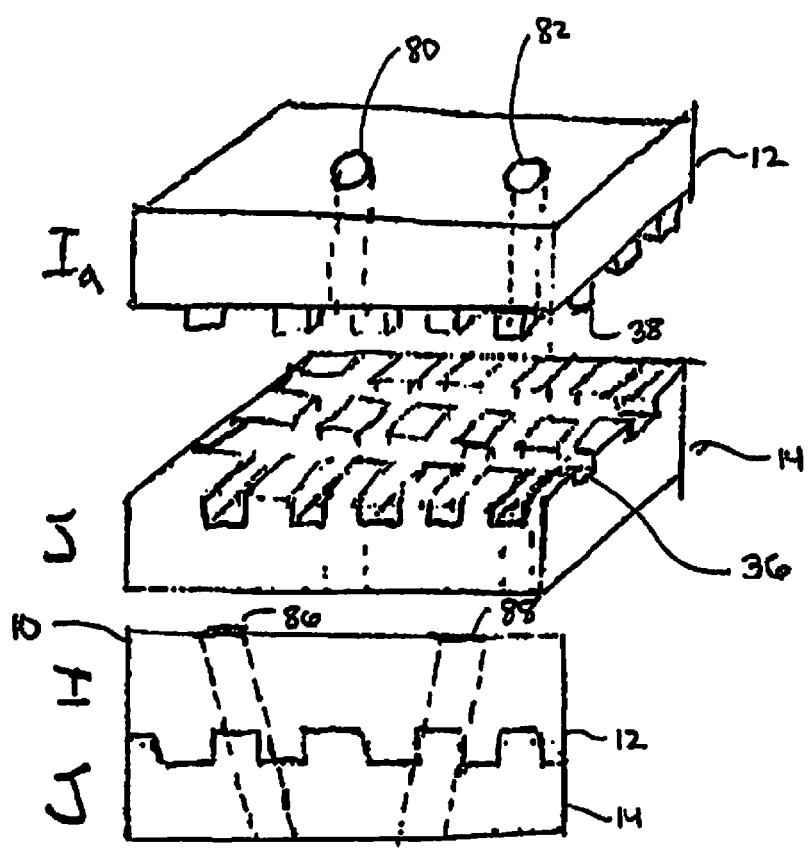
FIGS. 10A-10C illustrate different views of a multi-layered implant having a mating interface comprising waffle-pattern features according to some embodiments.

FIGS. 10A-10C illustrate different views of a multi-layered implant having a mating interface comprising waffle-pattern features according to some embodiments. FIG. 10A illustrates an upper layer 12 having a bottom mating face comprised of a plurality of square or rectangular protrusions 38 with grooves in between that form a waffle-pattern. FIG. 10B illustrates a lower layer 14 having an upper mating face including square or rectangular protrusions 38 and grooves in between that is designed to complement the mating face of the upper layer 12. The multi-layered implant can include vertical bore holes 80, 82, as shown in FIGS. 10A and 10B, or diagonal bore holes, as shown in FIG. 10C, for receiving a fixation member.

Figure 11A:
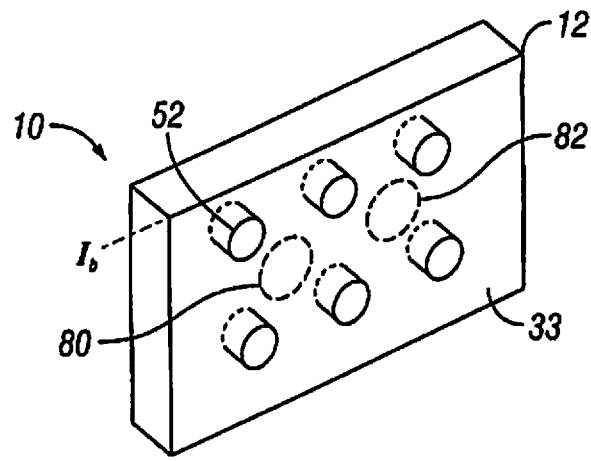
FIGS. 11A-11C illustrate different views of a multi-layered implant having a mating interface comprising geometrical inserts according to some embodiments.
Figure 11B:
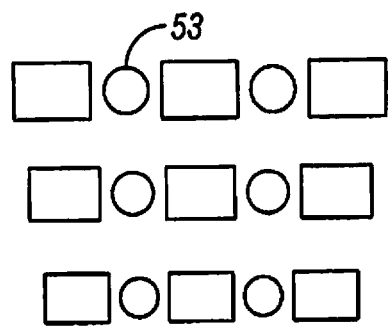
Figure 11C:
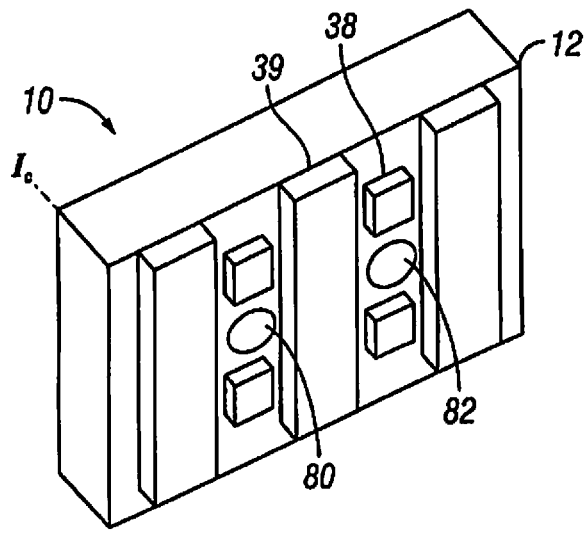

FIGS. 11A-11C illustrate different views of one or more layers of a multi-layered implant 10 having a mating interface comprising geometrical inserts according to some embodiments. FIG. 11A illustrates representative layer $I_b$, which includes a mating face 33 having one or more cylindrical inserts 52 protruding from a surface. The cylindrical inserts 52 can be inserted into apertures 53 of a corresponding mating face, as shown in FIG. 11B. The cylindrical inserts advantageously serve as pegs that help to maintain and secure the multiple layers of the multi-layered implant together before and during implant.

FIG. 11C illustrates an alternative layer 12 of a multi-layered implant 10 having a mating interface comprising differently shaped geometrical inserts 38. The geometrical inserts 38 resemble square or rectangular features (similar to that shown in FIG. 4), and can be inserted into one or more apertures on a face of a complementary layer. As shown in FIG. 11C, the layer 12 also includes one or more block features 39 that extend along a height of the layer 12. By combining different engaging features, such as the geometrical inserts 38 and the block features 39, this strengthens the ability to interlock two layers of a multi-layered implant, thereby helping to secure the implant during use.

FIGS. 12A-12C illustrate different views of a multi-layered implant including horizontal bore holes according to some embodiments. FIG. 12A illustrates a layer 12 having one or more horizontal bore holes 94, 96 that can be axially aligned with one or more horizontal bore holes 94, 96 in a complementary layer 14 (shown in FIG. 12B). The mating face 33 of layer 12 also comprises a plurality of channels or grooves 40 that are designed to receive complementary features (e.g., block features 39) that protrude from the mating face 37 of layer 14.

FIG. 12C illustrates a cross-sectional view of an implant 10 having two layers 12, 14 mated together and including horizontal bore holes 94, 96. The horizontal bore holes 94, 96 extend from an anterior side 7 to a posterior side 8 of the implant 10.

Figure 13A:
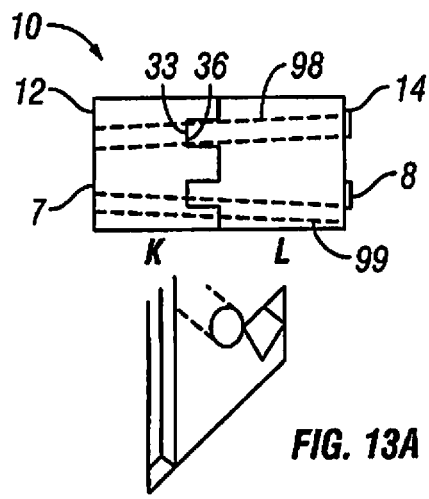
FIGS. 13A-13C illustrate different views of a multi-layered implant including diagonal bore holes according to some embodiments.
Figure 13B:
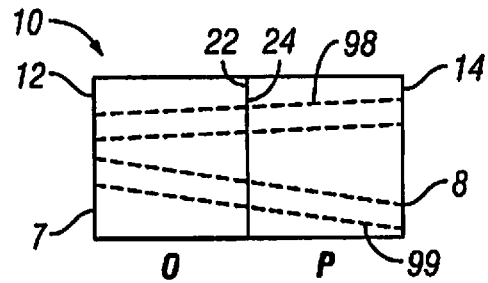
Figure 13C:
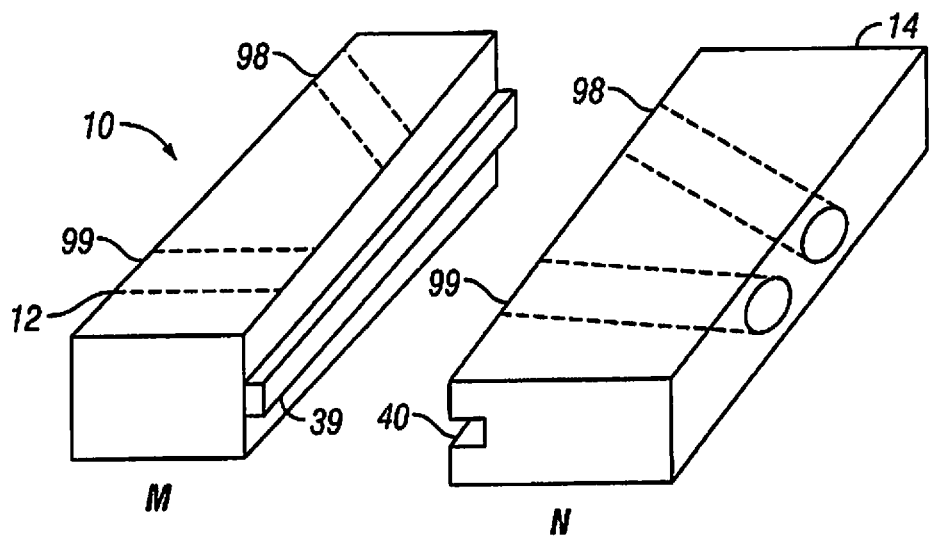

FIGS. 13A-13C illustrate different views of a multi-layered implant including diagonal bore holes 98, 99 according to some embodiments. The diagonal bore holes 98, 99 extend from an anterior face 7 to a posterior face 8. As shown in FIG. 13A, the multi-layered implant can include a first layer 12 having a first mating face 33 including one or more grooves for mating with a second mating face 36 of a second layer 14 having one or more protruding features. Alternatively, as shown in FIG. 13B, the multi-layered implant 10 can include a first layer 12 having a flat mating face 22 and a second layer 14 having a flat mating face 24 that form an interface. In yet another embodiment, as shown in FIG. 13C, the multi-layered implant 10 can include a first layer 12 having a first mating face with a block feature 39 that is capable of being inserted into a groove 40 formed in a second mating face of a second layer 14.

Figure 14:
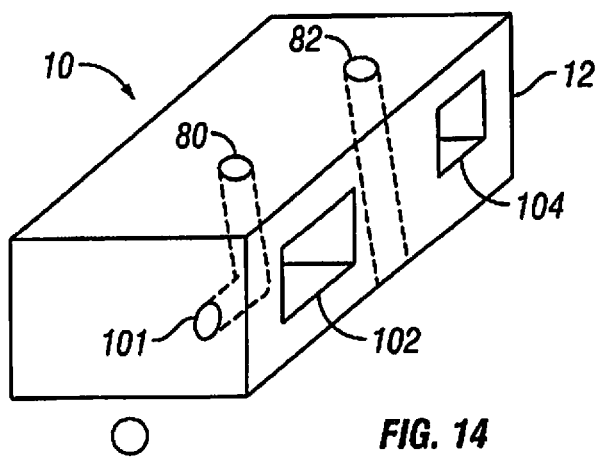
FIG. 14 is a top perspective view of a layer of a multi-layered implant having receiving windows according to some embodiments.

FIG. 14 is a top perspective view of a layer 12 of a multi-layered implant 10 having receiving windows 104 according to some embodiments. The receiving windows 104 are configured to receive one or more protruding features from a corresponding layer (not shown). Advantageously, the windows 104 have a sufficient height and width to accommodate a number of differently shaped protruding features. For example, while the windows 104 are rectangular shaped and can accommodate complimentary rectangular features, the windows 104 can also accommodate one or more cylindrical features. As shown in FIG. 14, the layer 12 also include vertical bore holes 80, 82 and a horizontal bore hole 101 that extends along a length of its longitudinal axis. The combination of different oriented bore holes advantageously allows for fixation members (e.g., pins) to be placed in the most desirable areas to support the mating of the different layers of the implant.

Figure 15:
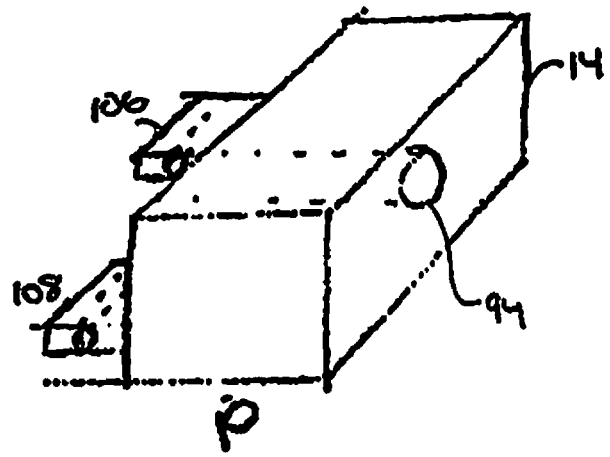
FIG. 15 is top perspective view of a complementary layer to the layer in FIG. 14.

FIG. 15 is top perspective view of a complementary layer 14 to the layer 12 in FIG. 14. Layer 14 includes two large rectangular inserts 106, 108 that can fit within the windows 102, 104 of the layer 14. The sides of the inserts 106, 108 can be flush against the sidewalls of the windows 102, 104. As shown in FIG. 15, layer 14 can include a horizontal bore hole 94 that is aligned along a length of a width of the layer 14.

Figure 16:
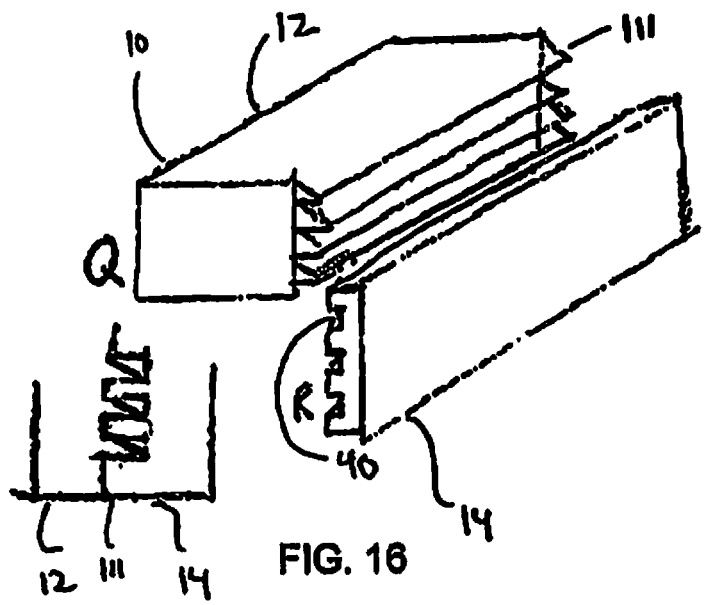
FIG. 16 illustrates different views of a multi-layered implant including a layer with a mating face including angled protrusions according to some embodiments.

FIG. 16 illustrates different views of a multi-layered implant 10 including a layer 12 with a mating face including protruding angled features 111 according to some embodiments. The protruding angled features 111 can fit into grooves 40 that are formed in a second layer 14, thereby forming a secure implant. In some embodiments, the grooves 40 are angled to complement the angled features 111. In other embodiments, the grooves 40 are not angled and simply receive and maintain the angled features 111 therein.

Figure 17:
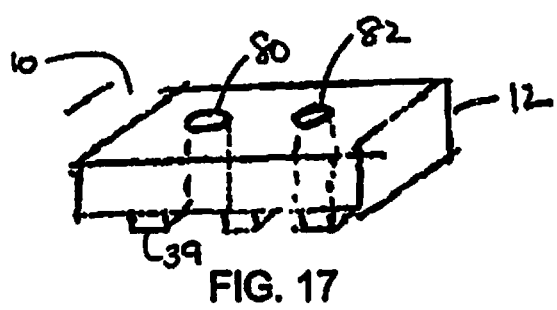
FIG. 17 is a top perspective view of a layer of a multi-layered implant comprising block features according to some embodiments.

FIG. 17 is a top perspective view of a layer 12 of a multi-layered implant 10 comprising block features 39 according to some embodiments. The block features 39 are configured to be received in grooves 40 formed in a complementary layer 14 (shown in FIG. 18).

Figure 18:
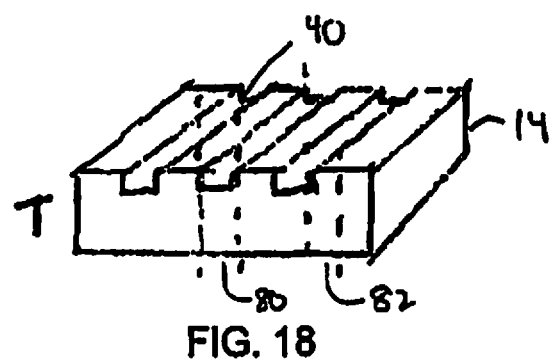
FIG. 18 is a top perspective view of a complementary layer to the layer in FIG. 17.

FIG. 18 is a top perspective view of a complementary layer 14 to the layer in FIG. 17. Layer 14 includes a plurality of grooves 40 for receiving the block features 39. In addition, as shown in FIG. 18, the vertical bore holes 80, 82 need not be symmetrical along the width of the layer 14 body. One vertical bore hole 80 extends through a groove 40, while the other vertical bore hole 82 extends through a wall adjacent to the groove 40.

Figure 19:
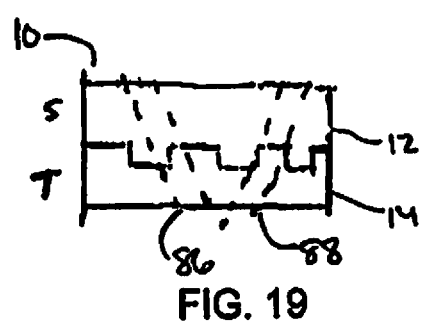
FIG. 19 is a cross-sectional view of a multi-layered implant having diagonal bore holes formed therein.

FIG. 19 is a cross-sectional view of a multi-layered implant 10 having two layers 12, 14 with diagonal bore holes 86, 88 formed therein. The diagonal bore holes 86, 88 extend through the interface formed by two faces of layers 12, 14.

FIGS. 20A-31F illustrate different implants having superior and/or inferior faces with surface features, such as teeth or ribs. While such implants are illustrated as being single-bodied, in some embodiments, the spacers are multi-pieced and can include any of the mating features/bore-holes described above. In addition, in some embodiments, the superior and inferior faces can be straight and substantially parallel to one another. In other embodiments, the superior and/or inferior faces can be curved (e.g., convex or concave). In addition, in some embodiments, each of the illustrated implants can have bodies that are angled to reflect the natural lordosis in a spine. In some embodiments, the implant bodies have angles between 2 degrees and 50 degrees, or 1 degree and 25, degrees relative to an axis that runs through the body of the implant, such as a midplane.

FIGS. 20A-20D illustrate different views of an implant 200 having teeth 232 according to some embodiments. The implant 200 can be inserted, for example, in the cervical area of a spine. The implant 200 includes a concave surface 206 in opposition to a convex surface 204 separated by a pair of sidewalls 208, 209. The implant 200 includes a superior face 216 and an opposing inferior face 218, which are substantially parallel. In other embodiments, the superior face 216 and/or inferior face 218 can be curved or angled such that the two faces are not substantially parallel.

The superior and/or inferior faces 216, 218 can include a plurality of teeth 232 for providing a friction surface against adjacent vertebrae. In some embodiments, the teeth 232 of similar height, while in other embodiments, the teeth 232 can have varying height across the body of the implant. The teeth can be three-sided, four-sided, six-sided or any other geometrical configuration. In some embodiments, the teeth are saw-tooth shape and include at least one surface that is substantially perpendicular to a surface of the implant.

A central hole 219 can be formed in the body of the implant 200 to receive a plug 210, such as in FIG. 20B. While the central hole 219 is illustrated as being circular, in other embodiments, the central hole 219 is square, rectangular, trapezoidal, tear shaped, or any other shape. In some embodiments, the central hole 219 has a geometry including one or more edges. In some embodiments, the implant 200 body can be formed of cortical material, while the inner plug 210 can be formed of cancellous material.

As shown in FIGS. 20B and 20D, the implant 200 can include one or more slots 260 configured to be grasped by an insertion instrument. While the slots 260 are formed on the sidewalls 208, 209 of the implant 200, in other embodiments, slots 260 can be formed on other parts of the implant body, such as on a superior 216 and/or inferior surface 218.

In addition to the features discussed above, the implant 200 can include a leading edge 240. In some embodiments, the leading edge 240 serves as distraction surface that helps to distract one or more vertebral bodies while the implant 200 is inserted into a disc space. In some embodiments, the leading edge 240 comprises smooth, tooth-free zones that are formed on the superior 216 and/or inferior surface 218 of the implant 200. As shown in FIG. 20D, the leading edge 240 can be angled or tapered such that the implant 200 is bullet-nose or wedge shaped.

FIGS. 21A-21D illustrate different views of an alternative implant 300 having teeth 232 according to some embodiments. The implant 300 can be inserted, for example, in a lumbar region of the spine via an anterior approach. The implant 300 can include two convex surfaces 332, 334 with sidewalls 308, 309 formed in between. The implant 300 further includes a superior surface 316 and an inferior surface 318. As shown in FIG. 21B, the superior surface 316 and/or the inferior surface 318 can have some slight curvature. In some embodiments, both the superior surface 316 and the inferior surface 318 include one or more teeth 232 to assist in providing a frictional zone against adjacent vertebral bodies.

As shown in FIG. 21A, the implant 300 can include a central hole 319. Unlike the central hole 219 in FIG. 20B, the central hole 319 in the present implant 300 is not filled with a cancellous bone plug. In some embodiments, the central hole 319 can be configured to receive bone graft material, which can assist in spinal fusion in between two vertebrae.

In some embodiments, the implant 300 can also include a leading edge 340 which is formed at the convergence of the superior surface 316 and inferior surface 318. The leading edge 340 can comprise smooth, tooth-free zones that serve to advantageously distract vertebral bodies during implantation.

As shown in FIG. 21B, leading edge 340 can be angled such that a portion of the implant 300 is bullet-nosed or wedge shaped.

In some embodiments, the implant 300 can also include slots 324 that are formed on the superior and/or inferior surfaces 316, 318 of the implant. In some embodiments, an insertion instrument can be used to grip the slots 324, thereby helping to facilitate the insertion of the implant in a vertebral space. In other embodiments, the slots 324 can receive one or more portions of a distraction instrument to assist in the distraction of adjacent vertebrae during implantation. In some embodiments, the insertion instrument can be an instrument separate from a distraction instrument. In other embodiments, the insertion instrument can include a distractor function, and can advantageously distract vertebrae while simultaneously inserting an implant.

Figure 22A:
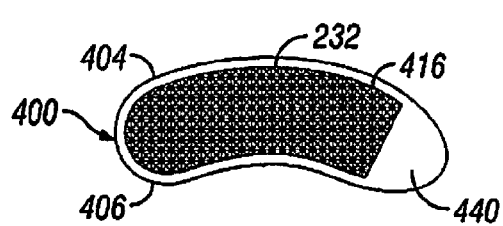
FIGS. 22A-22D illustrate different views of an alternative implant having teeth according to some embodiments.
Figure 22B:
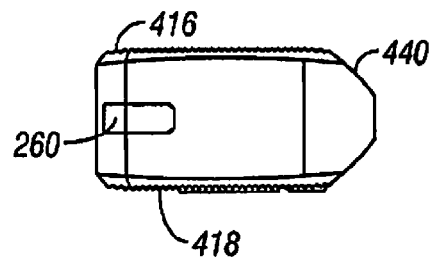
Figure 22C:
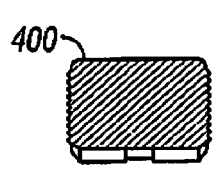
Figure 22D:
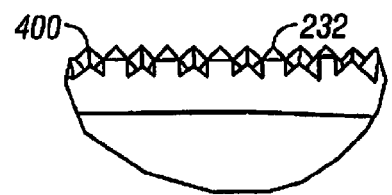

FIGS. 22A-22D illustrate different views of an alternative implant 400 having teeth 232 according to some embodiments. The implant 400 can be inserted, for example, in a lumbar region of the spine via a transforaminal approach. The implant includes a superior surface 416 and an inferior surface 418 that include teeth 232. As shown in FIG. 22A, the teeth need not extend entirely across the body of the implant 400; rather, a tooth-free region can be formed around the teeth 232. The implant 400 can include a convex surface 404 opposite a concave surface 406. The convex surface 404 and concave surface 406 can be substantially parallel, while in other embodiments, the convex surface 404 and concave surface 406 are not substantially parallel. As shown in FIG. 22C, the implant 400 can have a rectangular cross-sectional area.

In some embodiments, the implant 400 can include a slot 260. The slot 260 can be formed on the convex surface 404 and or concave surface 406, and can be configured to receive an insertion instrument to assist in delivery of the implant into an intervertebral space. In addition, as in previously discussed implants, the implant 400 can include a tooth-free, leading edge 440.

Figure 23A:
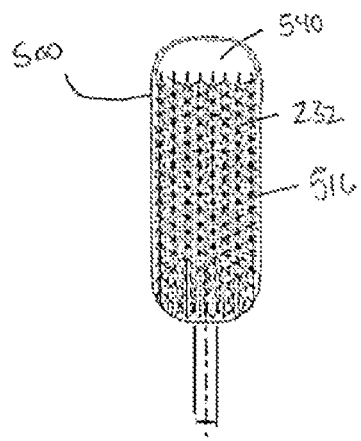
FIGS. 23A-23E illustrate different views of an alternative implant having teeth according to some embodiments.
Figure 23B:
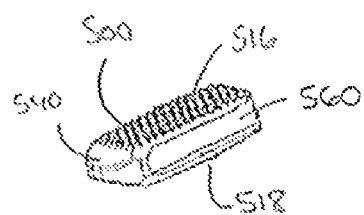
Figure 23C:
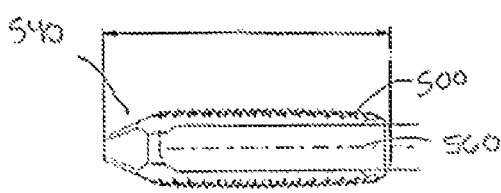

FIGS. 23A-23E illustrate different views of an alternative implant 500 having teeth according to some embodiments. The implant 500 can be inserted, for example, in a lumber region of the spine via a posterior approach. The implant 500 can have a substantially flat superior surface 516 that opposes a substantially flat inferior surface 518. In some embodiments, the implant 500 can be flat in a medial-lateral direction, but can include a radius of curvature in the anterior-posterior direction. Each of the superior surface 516 and/or inferior surface 518 can include teeth 232 for contacting vertebral bodies. As shown in FIG. 23C, the implant 500 can also include a leading edge 540.

As shown in FIGS. 23B and 23C, the implant 500 can include a large slot 560 for receiving a portion of an insertion instrument. In some embodiments, the slot 560 advantageously extends along a majority of the length of the implant 500, thereby creating a large surface area for receiving a portion of an insertion instrument.

Figure 23D:
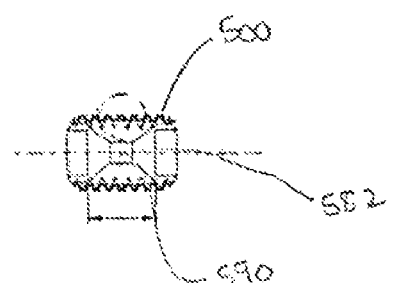
Figure 23E:
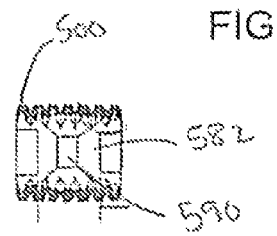
Figure 24A:
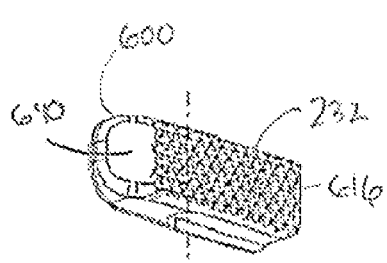
FIGS. 24A-24E illustrate different views of an alternative implant having teeth according to some embodiments.
Figure 24B:
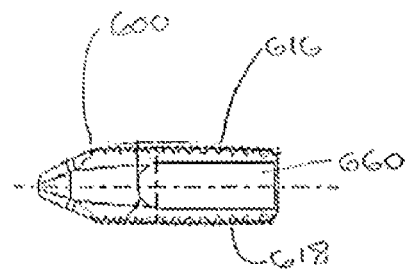
Figure 24C:
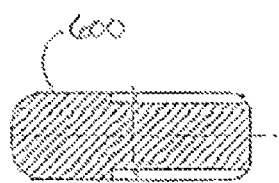
Figure 24D:
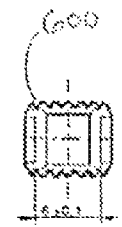
Figure 24E:
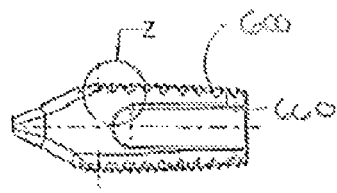

FIGS. 23D and 23E illustrate alternative rear views of the implant 500. As shown in these figures, in some embodiments, a posterior portion of the implant 500 can have angled, tapered surfaces 582 that converge at a flat face 590. In some embodiments, the posterior face 590 can have a length and height that is substantially different from the length and height of a face along an anterior portion of the implant 500.

FIGS. 24A-24E illustrate different views of an alternative implant 600 according to some embodiments. The implant 600 can be inserted, for example, in a lumbar region of the spine via a posterior approach. The implant 600 shares many similar features as the implant in FIG. 23A, including a superior face 616 and inferior face 618 including teeth 232, a leading edge 640 that is angled, and a slot 660 that extends substantially along a majority of the length of the body of the implant 600.

Figure 25A:
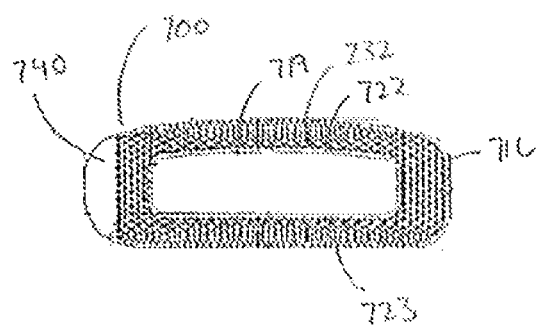
FIGS. 25A-25E illustrate different views of an alternative implant having teeth according to some embodiments.
Figure 25B:
Figure 25C:
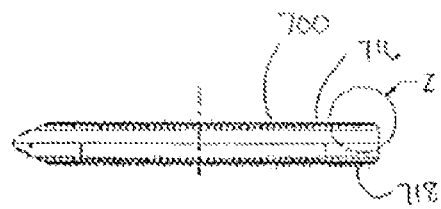
Figure 25D:
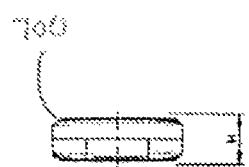

FIGS. 25A-25E illustrate different views of an alternative implant 700 having teeth 232 according to some embodiments. The implant 700 can be inserted, for example, in a lumbar region of the spine via a lateral approach. The implant includes a superior face 716 and an inferior face 718, each including a plurality of teeth 232 formed thereon. As shown in FIG. 25C, the superior face 716 and inferior face 718 can be substantially flat and planar, while in other embodiments, the superior face and/or inferior face can be curved. The implant 700 can also include a tooth-free, leading edge 740.

In some embodiments, the implant 700 can include a hole 719 extending from a superior face 716 to an inferior face 718, as shown in FIG. 25A. While the hole 719 is illustrated as a polygon having one or more curved or straight edges, in other embodiments, the hole 719 is round. As shown in FIG. 25A, the hole 719 can include two sidewalls 722 and 723 that extend along a majority of the length of the implant 700. By having such a lengthy hole, bone graft can advantageously be inserted and grow along a substantial portion of the implant, thereby aiding in bone fusion processes. In some embodiments, the two sidewalls 722, 723 substantially match the sidewalls of the implant 700.

Figure 25E:
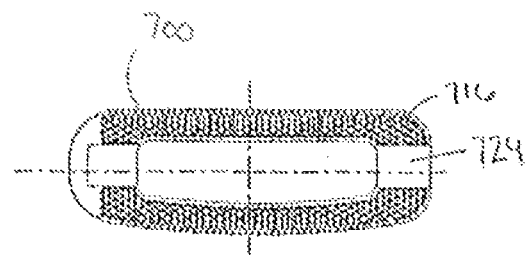

In some embodiments, as shown in FIG. 25E, implant 700 can include one or more slots 724 on a superior surface 716 and/or inferior surface 718. The slots 724 can be configured to receive one or more instruments, such as insertion or distraction instruments, to assist in the implantation of the implant 700.

In contrast to the implants in FIGS. 20A-25E, the implants in FIGS. 26A-31F include ribs or ridges, rather than teeth. These implants are now discussed.

FIGS. 26A-26D illustrate various embodiments of an implant 1200 having ridges 236. The implant 1200 can be inserted, for example, in a cervical region of the spine. The implant 1200 can include a convex surface 204 and a concave surface 206 with sidewalls therebetween.

Figure 26A:
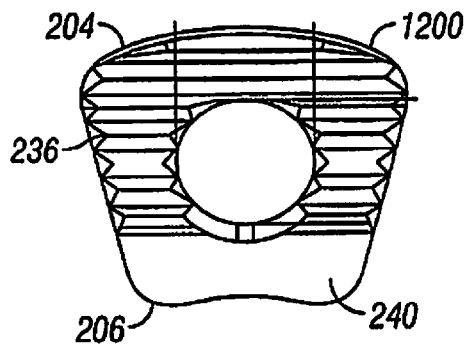
FIGS. 26A-26D illustrate different views of an implant having ridges according to some embodiments.

The implant 1200 can include a plurality of ridges 236 formed on a superior surface 216 and/or inferior surface 218. In some embodiments, the ridges 236 are formed continuously across a surface of the implant 1200 (as shown in FIG. 26A), whereas in other embodiments, the ridges 236 are separated and have spaces in between. The implant 1200 can include a tapered leading edge 240, thereby forming a bullet-nose or wedge-shaped portion.

Figure 26B:
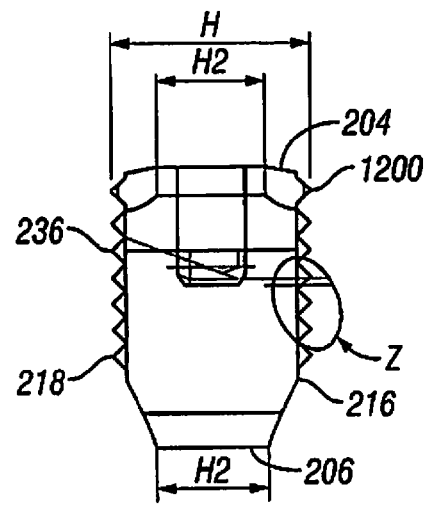
Figure 26C:
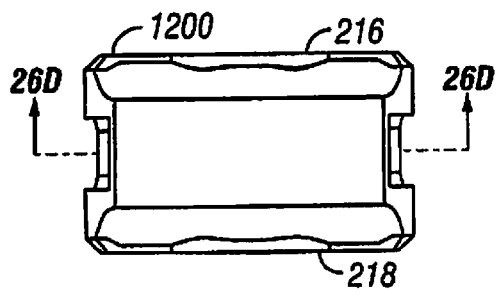
Figure 26D:
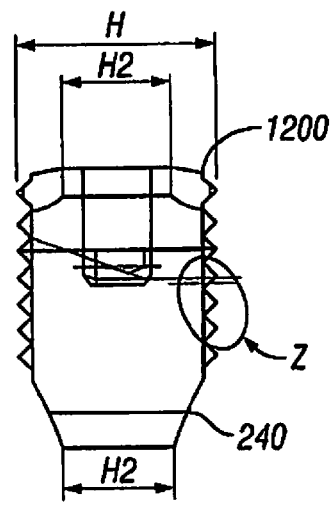

In some embodiments, as shown in FIG. 26B, the convex surface 204 can comprise a posterior face having a height H2. The concave surface 206 can also comprise an anterior face having a similar height H2. One skilled in the art will appreciate that the convex surface 204 can also be considered an anterior face, while the posterior face can be considered an anterior face, depending on the position of a user relative to the spine. In other embodiments, the anterior face and posterior face of the implant 1200 can be of differing heights.

Figure 27A:
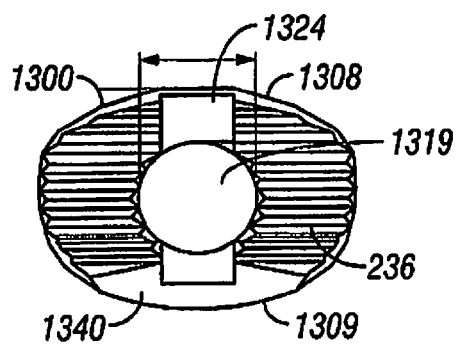
FIGS. 27A-27E illustrate different views of an alternative implant having ridges according to some embodiments.

FIGS. 27A-27E illustrate various embodiments of an alternative implant 1300 having ridges 236. The implant can be inserted, for example, in a lumbar region of the spine via an anterior approach. The implant 1300 includes a superior surface 1316 and an inferior surface 1318, each covered in part by one or more ridges 236. As shown in FIG. 27A, the implant 1300 can include a leading end 1340 which is smooth and not covered by ridges. In addition, the implant 1300 can include one or more slots 1324 that can be grasped by a distraction and/or insertion instrument to assist in inserting the implant into a vertebral space. The implant 1300 also includes a hole 1319 for receiving graft material. While the hole 1319 is illustrated as circular, in other embodiments, the hole 1319 is square, rectangular, trapezoidal or any other shape.

Figure 27B:
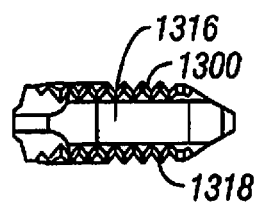
Figure 27C:
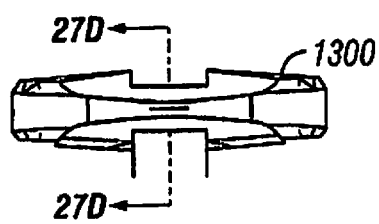

In some embodiments, as shown in FIG. 27B, the superior surface 1316 and the inferior surface 1318 are substantially parallel. In other embodiments, the superior surface 1316 and/or the inferior surface 1318 can be partially curved and/or angled (lordotic), such that the two surfaces are not substantially parallel. In some embodiments, an anterior face of the implant 1300 can be of similar height H2 to a posterior face of the implant 1300, as shown in FIG. 27B.

Figure 27D:
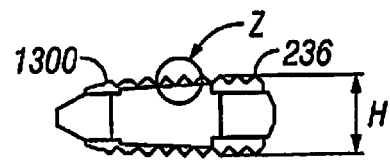
Figure 27E:

As shown in FIG. 27D, the ridges 236 formed on the implant can be substantially continuous. That is, there is a minimal if any gap or space between adjacent ridges. In other embodiments, the ridges 236 can be separated by a space and are not continuously formed.

FIGS. 28A-28E illustrate various embodiments of an alternative implant 1400 having ridges 236 that can be used, for example, in a lumbar region via a transforaminal approach. The implant 1400 includes a first sidewall 1404 that is opposite a second sidewall 1406. The first sidewall 1404 includes two concave surfaces 1414 and 1418. The second sidewall 1406 includes a third concave surface 1406. Advantageously, with the multiple concave surfaces, the implant 1400 is of a geometry that is desirable for different approaches, such as a transforaminal approach.

In addition to the features discussed above, the implant 1400 can also include one or more slots 1460 formed on one or more of the sidewalls 1404, 1406. The one or more slots 1460 can be grabbed by an insertion instrument.

Figure 29A:
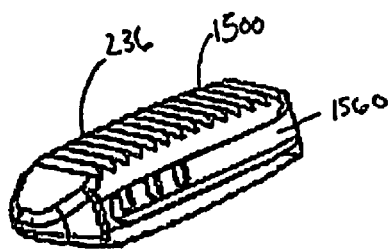
FIGS. 29A-29E illustrate different views of an alternative implant having ridges according to some embodiments.
Figure 29B:
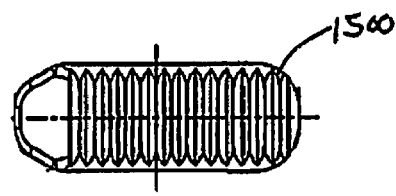
Figure 29C:
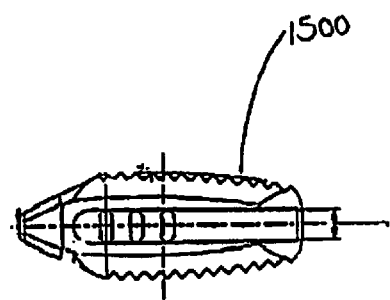
Figure 29D:
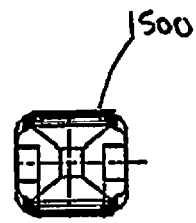
Figure 29E:
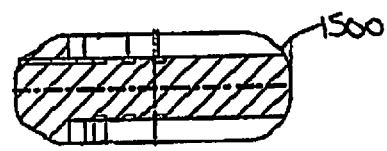

FIGS. 29A-29E illustrate various embodiments of an alternative implant 1500 having ridges 236 that can be used, for example, in a lumbar region of the spine via a posterior approach. The implant includes a pair of side channels 1560 for receiving an insertion instrument Advantageously, as shown in FIG. 29A, the side channels 1560 can extend along a majority of the length of the implant 1500, thereby providing a large grasping area for the insertion instrument.

Figure 30A:
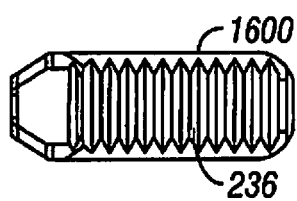
FIGS. 30A-30F illustrate different views of an alternative implant having ridges according to some embodiments.
Figure 30B:
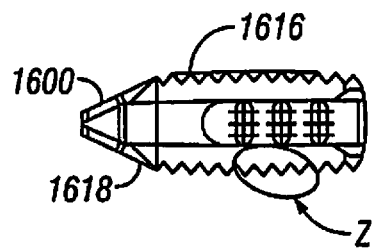
Figure 30C:
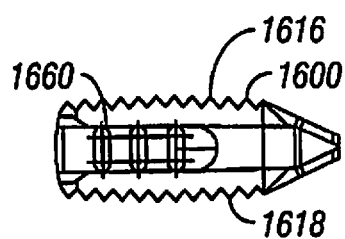
Figure 30D:
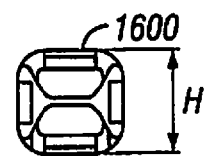
Figure 30E:
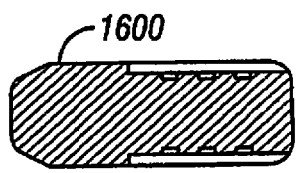
Figure 30F:
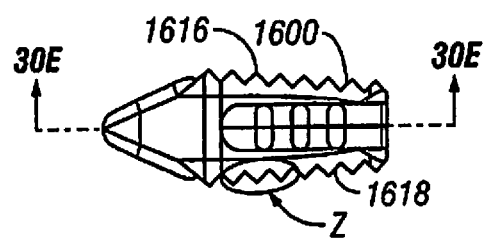

FIGS. 30A-30F illustrate various embodiments of an alternative implant 1600 having ridges 236 that can be used, for example, in a lumbar region of the spine via a posterior approach. The implant is similar to that shown in FIGS. 29A-29E, but includes a different footprint. While some of the embodiments illustrate an implant 1600 having a superior surface 1616 and an inferior surface 1618 that are parallel or minorly curved (FIG. 30B), other embodiments illustrate an implant 1600 having a superior surface 1616 and an inferior surface 1618 that are noticeably curved and form a lordotic structure (FIG. 30F).

Figure 31A:
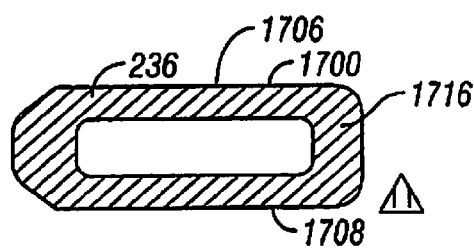
FIGS. 31A-31F illustrate different views of an alternative implant having ridges according to some embodiments.
Figure 31B:
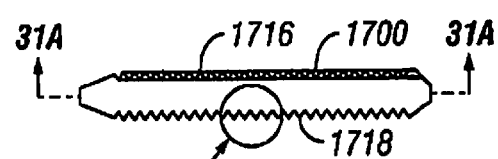
Figure 31C:
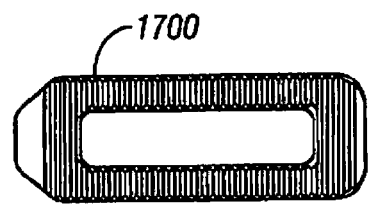
Figure 31D:
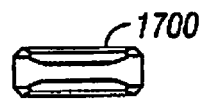
Figure 31E:
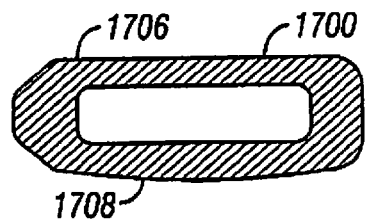
Figure 31F:

FIGS. 31A-31F illustrate various embodiments of an implant 1700 having ridges 236 that can be used, for example, in a lumbar region via a lateral approach. In some embodiments, the implant can include two parallel sidewalls 1706 and 1708 (FIG. 31A), while in other embodiments, the implant can include a straight sidewall 1706 that opposed a convex sidewall 1708 (FIG. 31E). In addition, in some embodiments, the implant 1700 can have substantially parallel superior and inferior surfaces 1716, 1718 (FIG. 31D), while in other embodiments, the implant 1700 can have a lordotic angled surface (FIG. 31F).

FIGS. 32A-44 illustrate additional embodiments of multi-piece implant assemblies. These embodiments are now described and are meant only to be illustrative. For example, while the implant assemblies in FIGS. 32A-44 do not illustrate horizontal bore holes, these implants may also include these features.

Figure 32A:
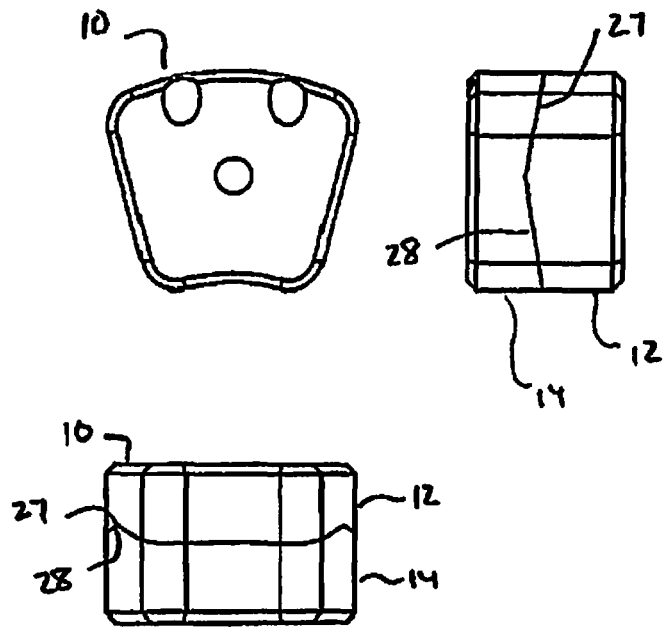
FIGS. 32A-32C illustrate different views of a multi-layered implant having various mating features according to some embodiments.
Figure 32B:
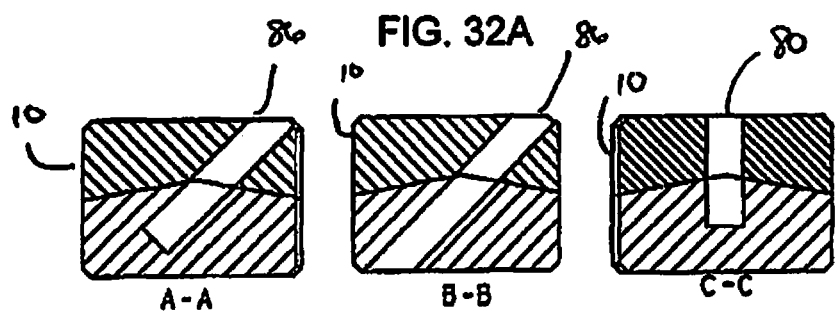
Figure 32C:
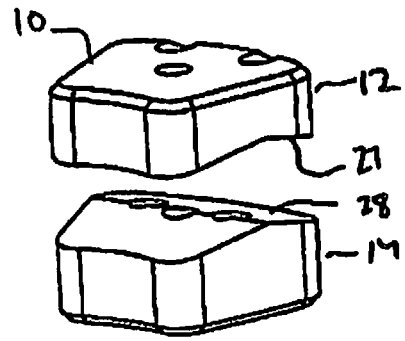

FIGS. 32A-32C illustrate embodiments of a multi-piece implant 10 having angled and/or curved mating faces 27, 28. Layer 12 includes an angled mating face 27 that mates with angled mating face 28 of layer 14. Advantageously, by having complementary features, this helps to keep the two layers 12, 14 of the implant 10 together.

As shown in FIG. 32B, diagonal bore holes 86 and/or vertical bore holes 80 can be introduced through the implant 10. The bore holes can extend complete through the implant, from a superior surface to an inferior surface. Alternatively, the bore holes can be blind, wherein a side of the bore hole is blocked by a surface of one of the layers 12, 14. By having blind bore holes, this advantageously prevents inadvertent removal or back-out of fixation members that are inserted through the holes.

Figure 33A:
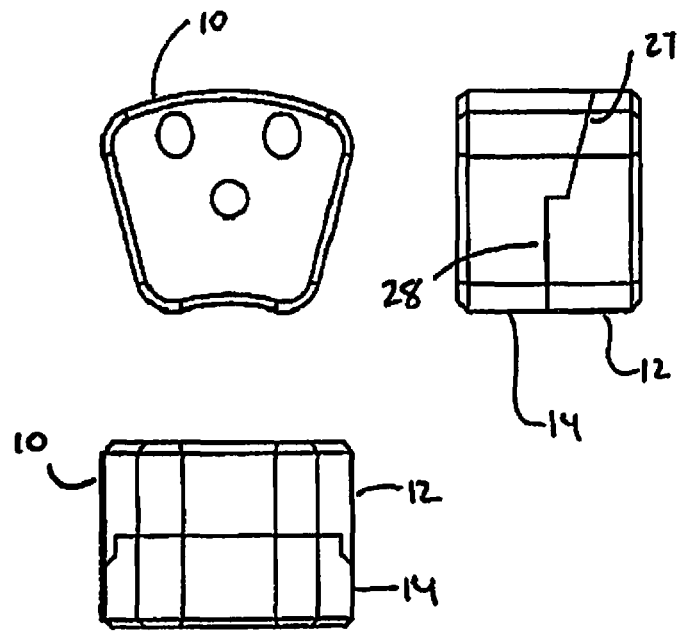
FIGS. 33A-33C illustrate different views of an alternative multi-layered implant having various mating features according to some embodiments.
Figure 33B:
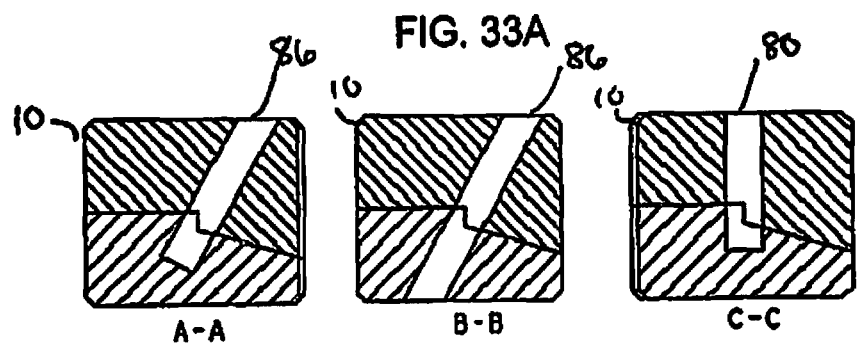
Figure 33C:
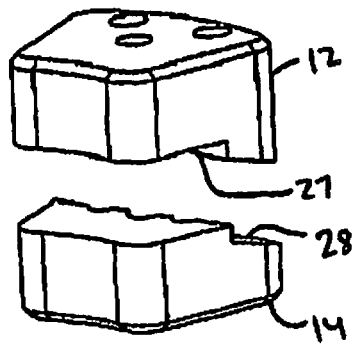

FIGS. 33A-33C illustrate some embodiments of a multi-piece implant 10 having zig-zagged mating faces 27, 28. Layer 12 includes a first zig-zagged mating face 27, while layer 14 includes a second zig-zagged mating face 28. As shown in FIG. 33C, each of the zig-zagged mating faces 27, 28 can include stepped features. The zig-zagged mating faces 27 and 28 complement each other, thereby helping to form a secure multi-piece implant.

As shown in FIG. 33B, the implant 10 can also include diagonal bore holes 86 and/or vertical bore holes 80 that extend across the interface of the two bodies 12 and 14. The bore holes 86 and 88 can extend completely through a superior surface to an inferior surface, or alternatively, can be blind bore holes as discussed above.

FIGS. 34A-34C illustrate some embodiments of a multi-piece implant 10 having curved mating faces 27, 28. As shown in the figures, the mating faces 27, 28 of the layers can be continuously curved without having any particular edge. The layers 12, 14 in the present embodiments can also include diagonal and/or vertical bore holes that are may or may not be blind.

FIGS. 35A-35C illustrate some embodiments of a multi-piece implant 10 having straight, jagged mating faces 27, 28. As shown in FIG. 35C, layer 12 can have a mating face 27 that is comprised of a single jagged step. Likewise, layer 14 can have a mating face 28 that is comprised of a complementary jagged step such that when layer 14 is pressed against layer 12, the two layers form a multi-piece implant. As in previously discussed embodiments, the implant 10 can include a variety of different bore holes that are continuous from a superior surface to an inferior surface, or blind.

Figure 36A:
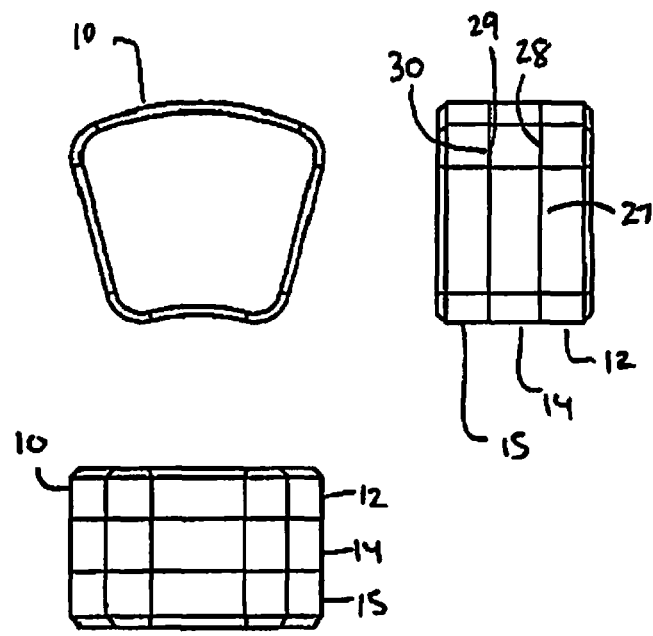
FIGS. 36A-36C illustrate different views of an alternative multi-layered implant having various mating features according to some embodiments.
Figure 36B:
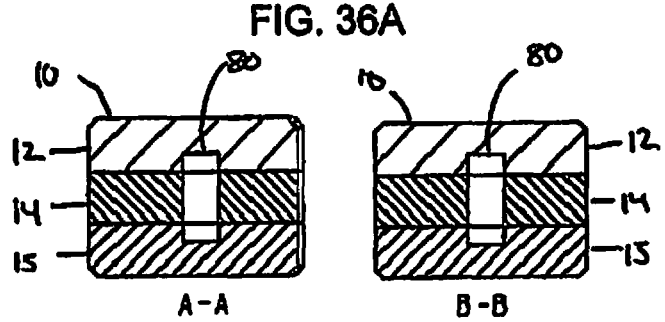
Figure 36C:
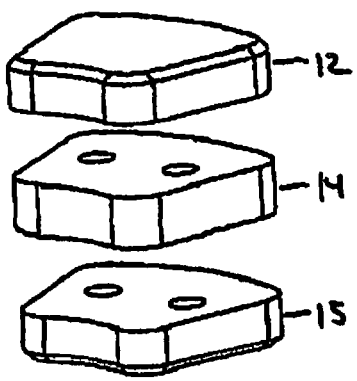

FIGS. 36A-36C illustrate some embodiments of a multi-piece implant 10 having at least three layers 12, 14, 15 with flat mating faces. Layer 12 includes a flat mating face 27 that forms an interface with flat mating face 28 of layer 14, while layer 15 includes a flat mating face 30 that forms an interface with flat mating face 29 of layer 14. In other embodiments, less than three layers (e.g., two) or greater than three layers (e.g., four or five) having flat mating faces can form a similar multi-piece implant.

As shown in FIG. 36B, the multi-piece implant 10 can incorporate a bore hole such as vertical bore hole 80. In some embodiments, the bore hole 80 will not extend through either a superior face or an inferior face, but rather, can have two blind ends, as shown in FIG. 36B. Advantageously, by having two blind ends, the bore hole 80 will be able to fix the multiple layers together, but will be prevented from inadvertently backing out of the implant during use.

Figure 37A:
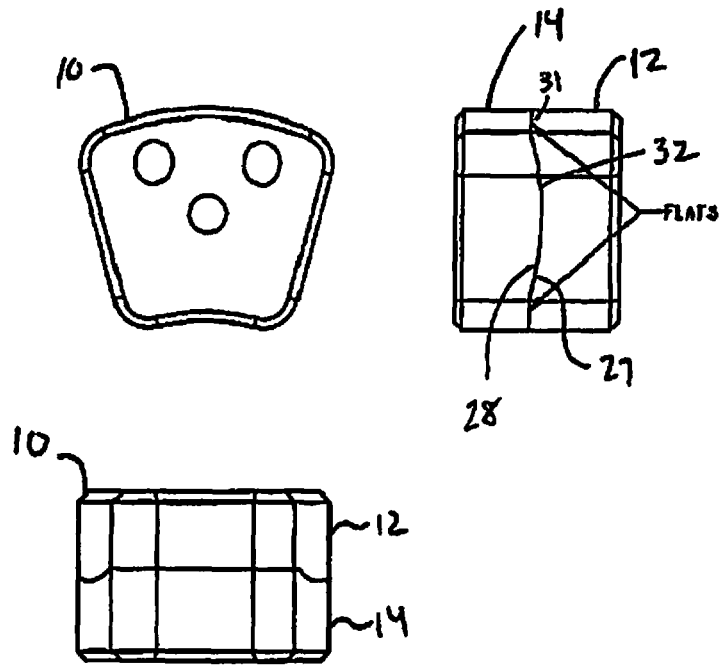
FIGS. 37A-37C illustrate different views of an alternative multi-layered implant having various mating features according to some embodiments.
Figure 37B:
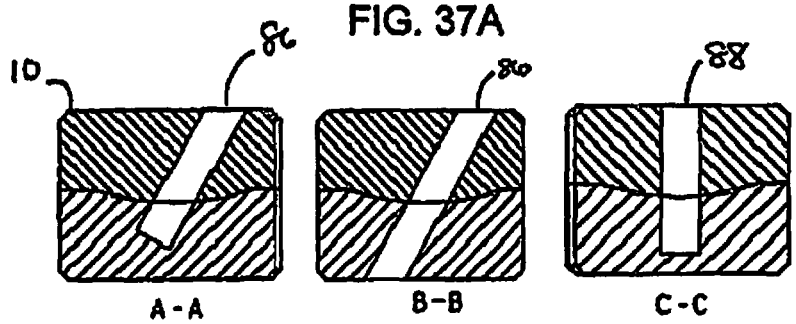
Figure 37C:
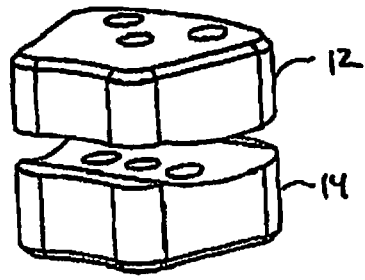

FIGS. 37A-37C illustrate some embodiments of a multi-piece implant 10 having layers with mating faces 27, 28 including a pair of exterior flats followed by a curved inner surface. As shown in FIG. 37A, layer 12 can include a mating face having a pair of exterior flats 31 and a curved inner surface 32 there between. Layer 14 can include a mating surface 28 that is complementary to the mating face 27, wherein it also includes flats and a curved inner surface. The multi-piece implant can include diagonal and vertical bore holes of different variations as shown in FIG. 37B.

Figure 38A:
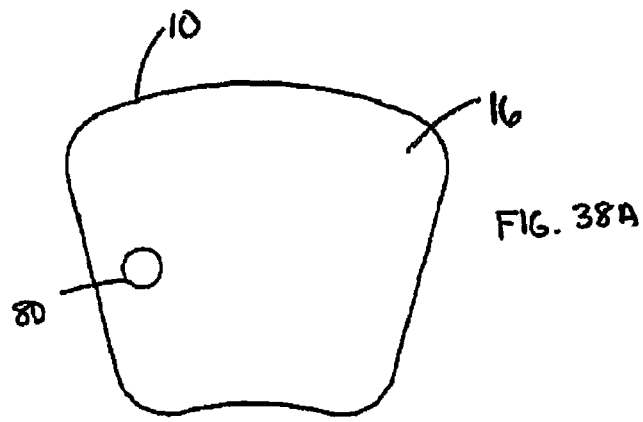
FIGS. 38A-38C illustrate some embodiments of a multi-piece implant having a pair of bore holes.
Figure 38B:
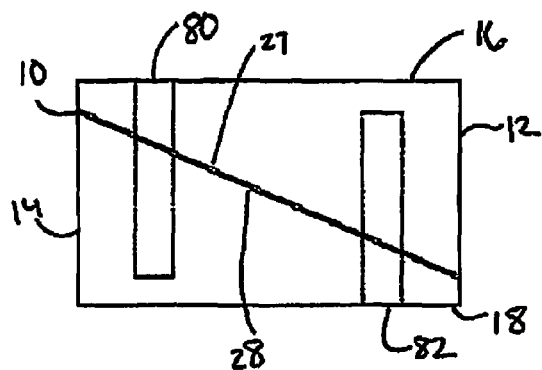
Figure 38C:
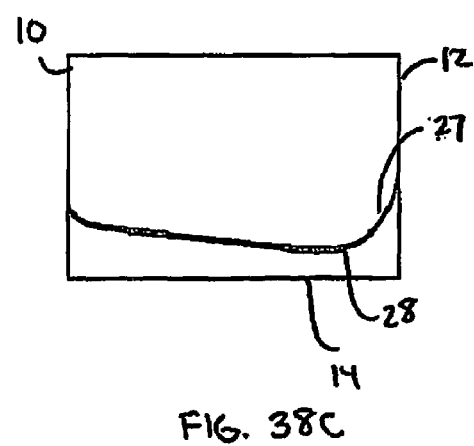

FIGS. 38A-38C illustrate some embodiments of a multi-piece implant 10 having a pair of bore holes 80, 82. As shown in FIG. 38B, each of the bore holes 80, 82 is blind. Accordingly, from a top view, only one bore hole 80 is visible in the superior surface, as shown in FIG. 38A. The bores 80, 82 each cross the interface formed by the contacting mating faces 27 and 28.

FIG. 38B illustrates a cross-sectional view of the implant 10 according to some embodiments. As shown in this view, the interface between the layer 12 and layer 14 is a flat surface. However, in alternative views, as show in the cross-sectional view of the implant 10 in FIG. 38C, the interface between layer 12 and layer 14 can also be curved in some portions.

Figure 39A:
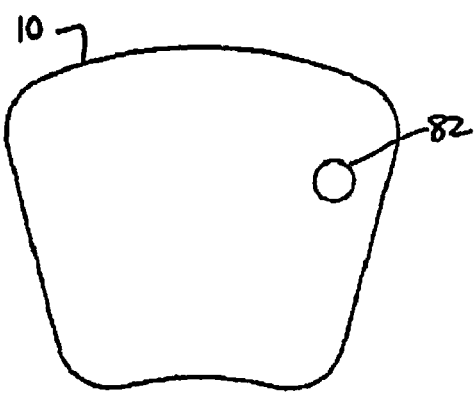
FIGS. 39A-39C illustrate some embodiments of an alternative multi-piece implant having a pair of bore holes.
Figure 39B:
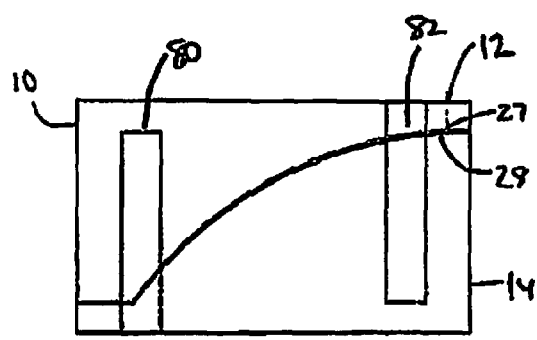
Figure 39C:
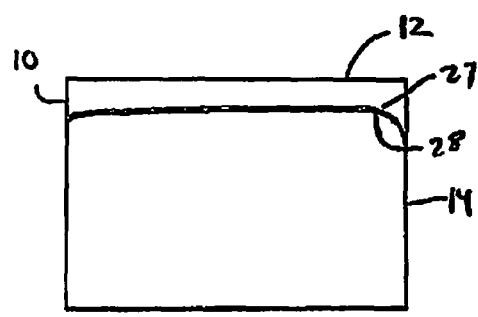

FIGS. 39A-39C illustrate some embodiments of an alternative multi-piece implant 10 having a pair of bore holes 80, 82. As shown in FIG. 39B, each of the bore holes 80, 82 is blind. Accordingly, from a top view, only one bore hole 82 is visible in the superior surface, as shown in FIG. 39A. The bores 80, 82 each cross the interface formed by the contacting mating faces 27 and 28.

FIG. 39B illustrates a cross-sectional view of the implant 10 according to some embodiments. As shown in this view, the interface between the layer 12 and layer 14 is not only flat, but also includes some curvature. The curved features of the interface are also shown in FIG. 39C.

Figure 40A:
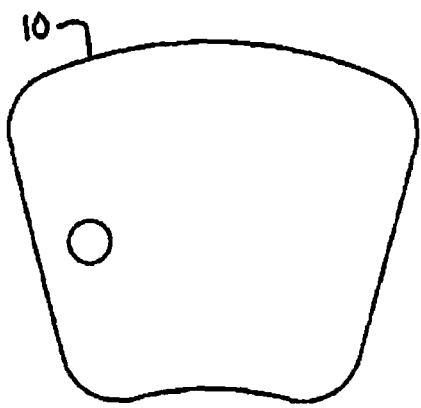
FIGS. 40A-40C illustrate some embodiments of an alternative multi-piece implant having a pair of bore holes.
Figure 40B:
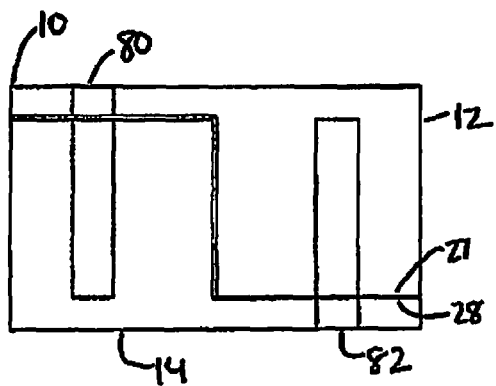
Figure 40C:
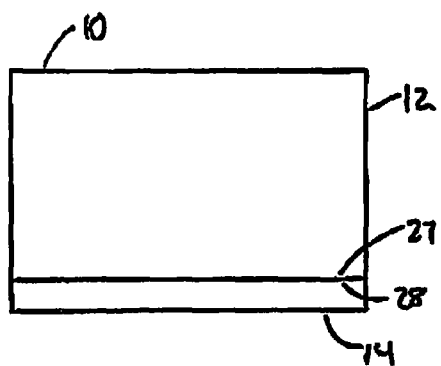

FIGS. 40A-40C illustrate some embodiments of a multi-piece implant 10 having a pair of bore holes 80, 82. The implant 10 is composed of two layers 12, 14. Each of the layers has a mating face 27, 28 that has a horizontally straight portion and a vertically straight portion, as shown in FIG. 40B. From a different cross-sectional view shown in FIG. 40C, the mating interface between layer 12 and layer 14 is flat.

FIGS. 41A-41C illustrate some embodiments of a multi-piece implant 10 having a pair of bore holes 80, 82. The implant is composed of two layers 12, 14, each having a flat mating face 27, 28. The implant 10 includes two vertical bore holes 80, 82.

Figure 42A:
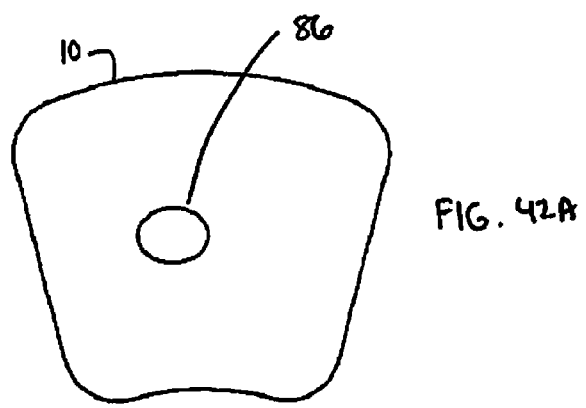
FIGS. 42A-42C illustrate some embodiments of an alternative multi-piece implant having a pair of bore holes.
Figure 42B:
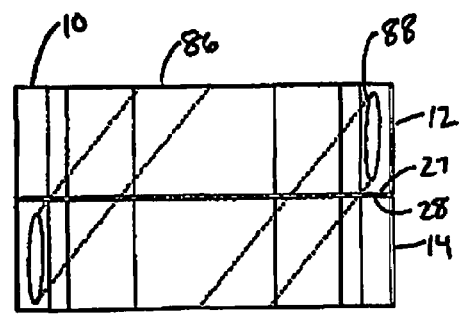
Figure 42C:
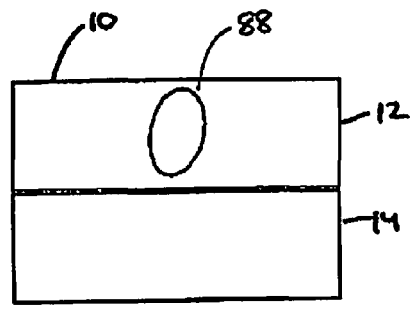

FIGS. 42A-42C illustrate some embodiments of a multi-piece implant 10 having a pair of diagonal bore holes 86, 88. Both of the bore holes 86, 88 are blind in that they do not extend completely through an implant. The implant 10 includes two layers 12, 14 having flat mating faces 12, 14, as shown from different viewpoints in FIGS. 42B and 42C.

Figure 43A:
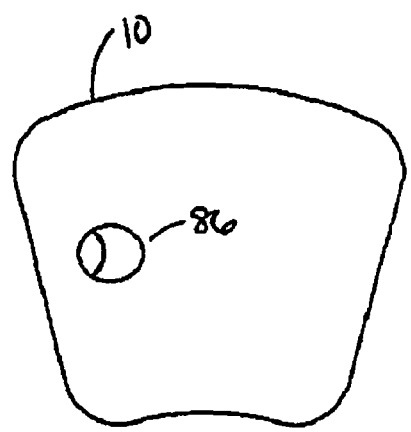
FIGS. 43A-43C illustrate some embodiments of an alternative multi-piece implant having a pair of bore holes.
Figure 43B:
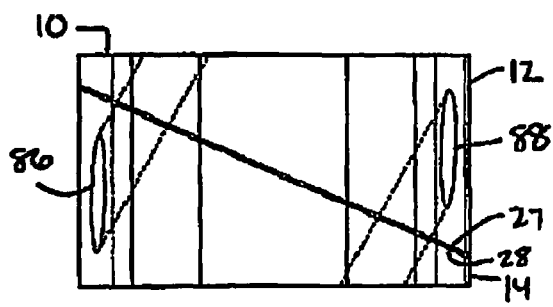
Figure 43C:
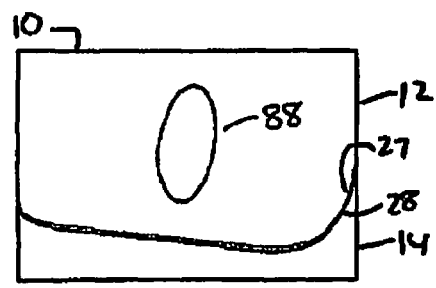

FIGS. 43A-43C illustrate some embodiments of a multi-piece implant 10 having a pair of diagonal bore holes 86, 88. In contrast to the previous embodiment, the current embodiment includes two layers 12, 14 having a mating interface that is angled, as shown in FIG. 43B. In addition, in some embodiments, portions of the mating interface can be curved, as shown in FIG. 43C.

Figure 44A:
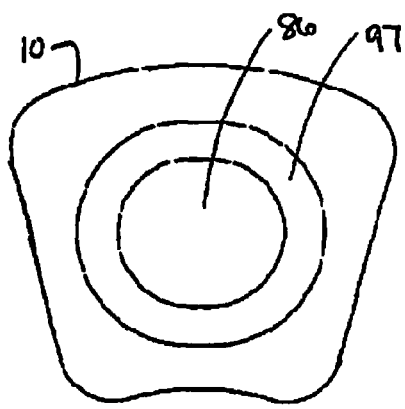
FIGS. 44A-44C illustrate some embodiments of multi-piece implant having an inner concentric member.
Figure 44B:
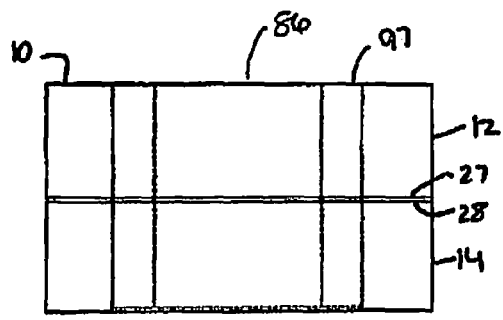
Figure 44C:
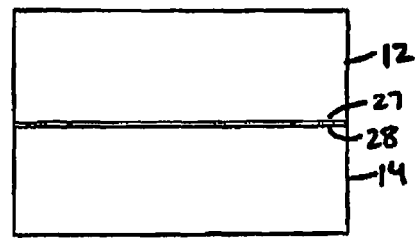

FIGS. 44A-44C illustrate some embodiments of a multi-piece implant 10 having an inner concentric member 97. As shown in FIG. 44A, the implant 10 is comprised of two separate layers 12 and 14. Each of the layers 12 and 14 includes an inner hole that aligns to form a single through hole when the two layers are pressed together, as shown in FIG. 44C. An inner concentric member 97 can be received through the single through hole, thereby advantageously helping to hold the implant in one piece. This design advantageously avoid the use of fixation members (e.g., pins), which can protrude from the body of the implant and/or inadvertently come loose within the system. In other embodiments, fixation members can be incorporated into the design.

Figure 45:
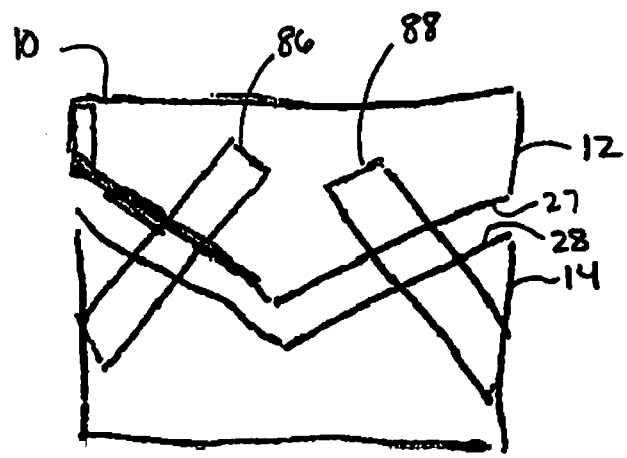
FIG. 45 is a cross-sectional view of a multi-piece implant having a pair of bore holes according to some embodiments.

FIG. 45 is a cross-sectional view of a multi-piece implant 10 having a pair of bore holes 86, 88 according to some embodiments. As shown in the illustration, the multi-piece implant 10 is composed of two layers 12, 14, each of which includes a v-shaped mating face 27, 28.

Figure 46:
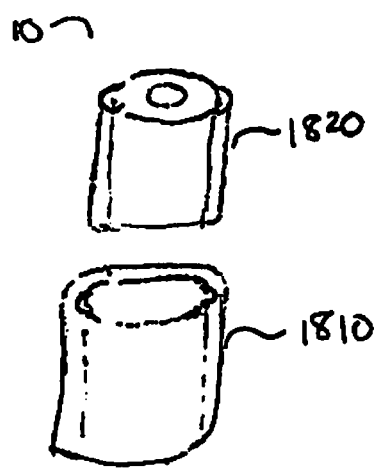
FIG. 46 illustrates a multi-piece implant having concentric components according to some embodiments.

FIG. 46 illustrates a multi-piece implant 10 having concentric components 1810, 1820 according to some embodiments. The implant 10 includes a first concentric outer member 1810 and a second concentric inner member 1820 that fits therein. In some embodiments, the inner member 1820 is slidable within the outer member 1810, thereby forming an implant for implanting in an intervertebral space.

Figure 47:
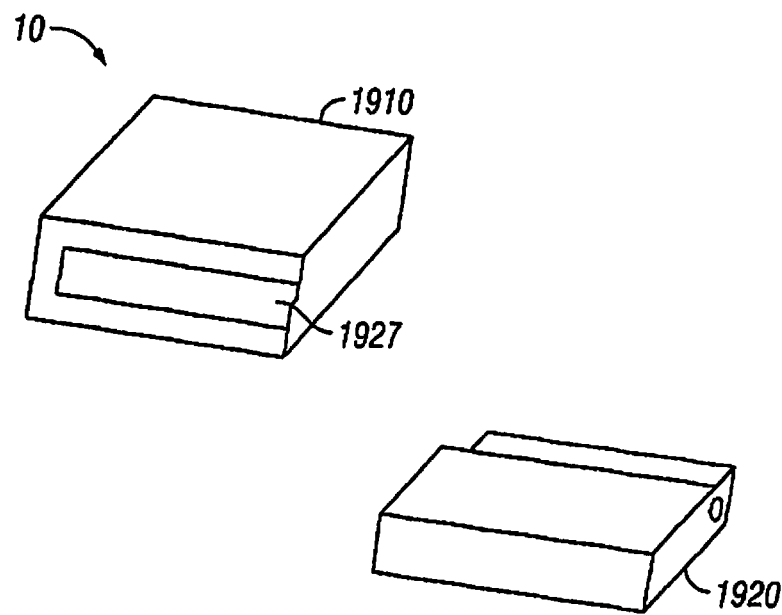
FIG. 47 illustrates a multi-piece implant having an insertable component according to some embodiments.

FIG. 47 illustrates a multi-piece implant 10 having an insertable component 1920 according to some embodiments. The implant 10 comprises a first layer 1910 including a slot 1927 that extends along a substantial portion of its width. The slot 1910 is configured to receive a second insertable layer 1920 that fits therein, thereby forming a multi-piece implant for implanting in an intervertebral space.

Figure 48:
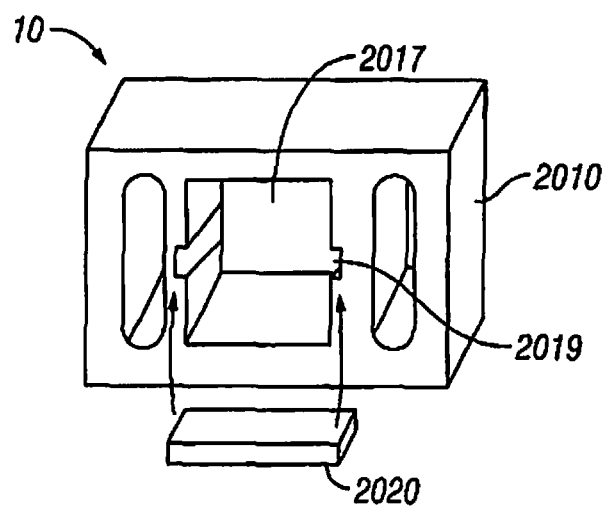
FIG. 48 illustrates an alternative multi-piece implant having an insertable component according to some embodiments.

FIG. 48 illustrates an alternative multi-piece implant 10 having an insertable component 2020 according to some embodiments. The implant 10 comprises a first member 2010 that includes an open chamber 2017. The open chamber 2017 includes one or more slots or recesses 2019 formed therein to receive an insertable component 2020. As shown in the figure, the insertable component 2020 can comprise a planar structure that is slidable into a corresponding recess 2019. While the illustrated embodiment shows a chamber 2017 having a single recess 2019 corresponding to a single insertable component 2020, in other embodiments, the chamber 2017 can include more than one slot. In some embodiments, the insertable component 2020 can be pinned to the open chamber 2017, thereby helping to further secure the multi-piece implant for use.

Figure 49A:
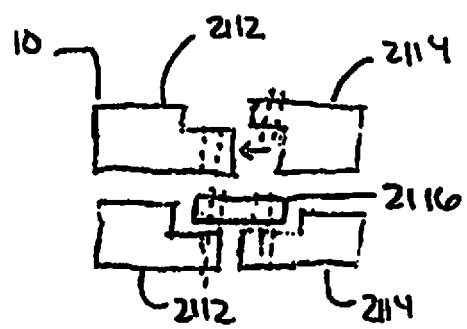
FIGS. 49A and 49B illustrate different embodiments of a multi-piece implant having components with engaging surfaces.
Figure 49B:
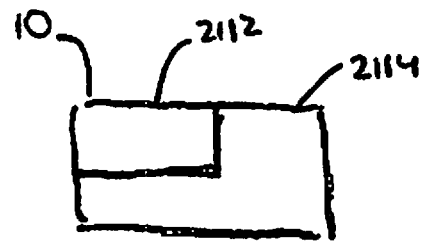

FIGS. 49A and 49B illustrate different embodiments of a multi-piece implant 10 having components with engaging surfaces. FIG. 49A illustrates two separate multi-piece implants 10 having components with engaging surfaces. Dashed lines represent optional pin holes. In some embodiments, the implant 10 can include a first component 2112 having a cut corner that engages a second component 2114 having a different cut corner to form a single-bodied implant. In other embodiments, the implant 10 can include a first component 2112 having a cut corner, a second component 2114 having a different cut corner, and a third component 2116 that completes the form implant 10.

FIG. 49B illustrates an embodiment of a multi-piece implant 10 having two separate components. The first component 2114 includes a cut rectangular corner, while the second component 2112 comprises a geometry that fits within the cut rectangular corner of the first component 2114.

Figure 50:
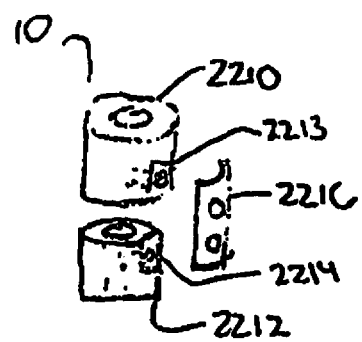
FIG. 50 illustrates a multi-piece implant having a connecting plate member according to some embodiments.

FIG. 50 illustrates a multi-piece implant 10 having a connecting plate member 2216 according to some embodiments. The implant 10 can comprise two cylindrical members 2210 and 2212. In alternative embodiments, the members 2210 and 2212 need not be cylindrical, but can be square, rectangular or any other shape. Each of the members 2210, 2212 include apertures 2213, 2214 for receiving a peg or rod of a connecting plate member 2216. The connecting plate member 2216 advantageously helps to hold the two cylindrical members 2210 and 2212 together, thereby forming an implant that is implantable in a vertebral space.

FIG. 51 illustrates a multi-piece implant 10 having threaded components according to some embodiments. The implant 10 can comprise a first component 2312 having an inner threaded section 2322 and a second component 2324 having a threaded protrusion 2324 that complements the inner threaded section 2322. The threaded components advantageously hold the implant together prior to, during and after implantation of the implant 10 in an intervertebral space.

FIGS. 52A and 52B illustrate a multi-piece implant having a concentric inner member according to some embodiments. FIG. 52A illustrates a cross-sectional view of an implant 10 having a concentric inner member 2408 that fits in an outer member 2414, while FIG. 52B shows a top view of the same implant 10. As shown in FIG. 52B, the outer member 2414 includes a central opening for receiving the inner member 2408, which resembles a ring. One or more bore holes can be formed through the inner and outer members to receive fixation devices for holding the implant together. While the bore holes are illustrated as diagonal bore holes 86, 88, 96, 98, in other embodiments, vertical and/or horizontal bore holes can be used to receive fixation devices.

Figure 53:
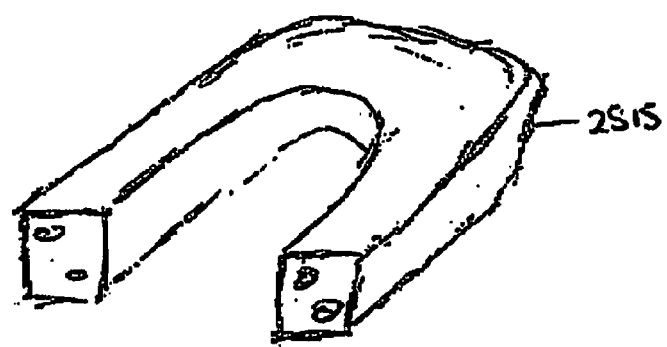
FIG. 53 illustrates an insertable member of a multi-piece implant according to some embodiments.

FIG. 53 illustrates an insertable member 2515 of a multi-piece implant according to some embodiments. The insertable member 2515 resembles a horse-shoe shape that can be received, for example, in a slot formed in a receiving member (not shown). As shown in this embodiment, various inserts of different shapes, geometries and sizes can be used to form a multi-layer implant.

Figure 54A:
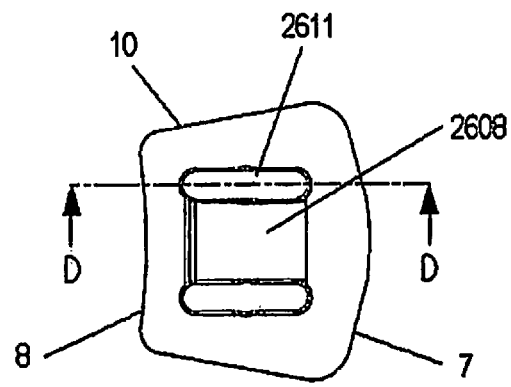
FIGS. 54A-54C illustrate an implant having shims according to some embodiments.
Figure 54B:
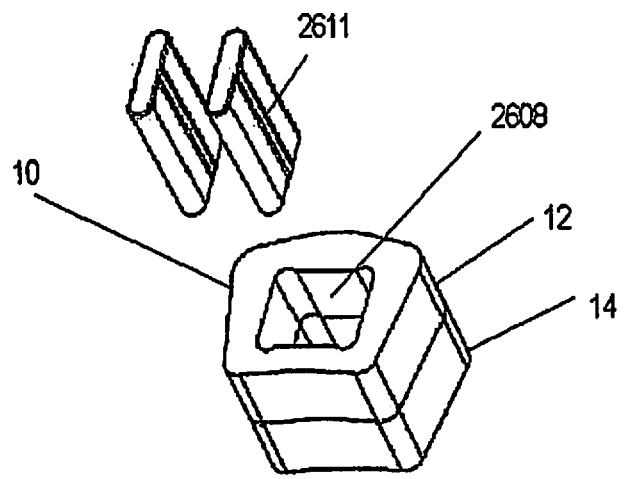
Figure 54C:
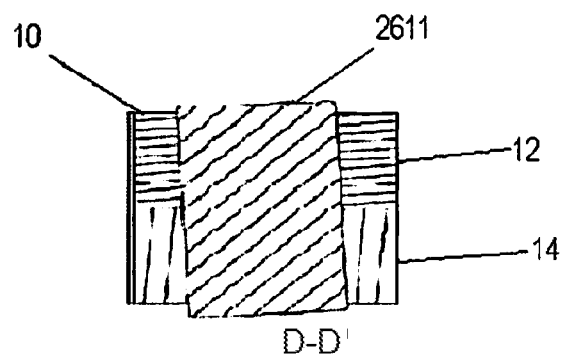

FIGS. 54A-54C illustrate an implant having shims according to some embodiments. The implant 10 comprises a body having an opening 2608 configured to receive one or more shim members 2611 therein. The implant can be sized and configured for use in any part of the vertebrae, including the lumbar, thoracic, and particularly, the cervical region.

The implant 10 comprises a body having an opening 2608 that is configured to receive bone material therein. The implant 10 can be a single-piece, or as in prior multi-piece implants described above, the implant 10 can include multiple layers. In some embodiments, the implant comprises a first layer 12 and a second layer 14. In other embodiments, the implant can be composed of three, four, five or more layers. In addition, while the layers 12 and 14 are stacked vertically, in other embodiments, the layers can be assembled horizontally or laterally.

As shown in FIGS. 54A-54C, the implant 10 can have a convexly curved anterior surface 7 and a concavely curved posterior surface 8. Such curvature can advantageously help to mimic the natural curvature of the space. In some embodiments, the convexly curved anterior surface 7 can have a curvature that is substantially smooth. In other embodiments, as shown in FIG. 54A, the curvature can include flat segments and even slight edges, so long as the overall surface is substantially curved. One skilled in the art will appreciate that the shape of the implant is not limited to the convexly curved anterior surface and concavely curved posterior surface. For example, in some embodiments, the implant 10 will have a convex surface opposed to a convex surface, or a convex surface opposed to a substantially flat surface. In addition, one skilled in the art will appreciate that the terms "anterior" and "posterior" are not limiting, and that the terms can be used to identify any opposing surface of the implant.

In some embodiments, the opening 2608 of the implant 10 extends from an upper superior surface to a lower superior surface of the implant. In some embodiments, the opening 2608 is composed of a first opening through the first layer 12 and a second opening through the second layer 14. In the illustrated embodiments, a first opening in the first layer 12 and a second opening through the second layer 14 can be substantially aligned to form the opening 2608. In other embodiments, a first opening in the first layer 12 and a second opening through the second layer 14 can be partially aligned and partially off-set.

As shown in FIGS. 54A and 54B, the opening 2608 in the implant 10 is symmetric, and includes a pair of opposing flat surfaces that transition into rounded corners. Advantageously, the rounded portions of the opening 2608 are configured to receive one or more shim members 2611 therein. While the illustrated embodiments show two shim members, the implant 10 can also be used with a single shim member, or three, four, five or more shim members.

Figure 57:
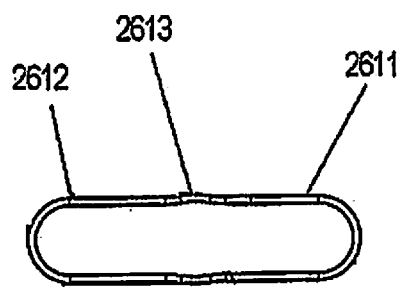
FIG. 57 illustrates a shim according to some embodiments.

The shim members 2611 are wedge-like members that are configured to be inserted (e.g., via friction or press-fit) through the opening 2608. Advantageously, insertion of the shim members 2611 into the opening 2608 helps to maintain the different layers 12 and 14 together and further provides structural support to the overall implant. In some embodiments, the shim members 2611 are oval or elliptical in shape, although other shapes and geometries are also possible. In addition, as shown in the shim member represented in FIG. 57, the shim members 2611 can include a small nub or protrusion 2613 that extends outwardly from a generally smooth, curved surface. The advantage of this nub 2613 is that it allows the shim to be more easily retained within the opening 2608 of the implant 10. In some embodiments, the shim members 2611 are composed of the same or similar material as the body of the implant 10. For example, the body of the implant 10 and the shim members 2611 can all be composed of allograft (e.g., cortical) bone. In other embodiments, the shim members 2611 are composed of a different material from the body of the implant 10. For example, the body of the implant 10 can be composed of a cortical bone, while the shim members 2611 can be composed of a harder synthetic material.

In some embodiments, the opening 2608 can be configured to receive the shim members 2611 at an angle relative to an interface of the first layer 12 and the second layer 14, as shown in FIG. 54C. Advantageously, by having shim members 2611 that are at an angle to an interface of the first layer and the second layer, this can help provide additional security for securing the first layer to the second layer during implantation. However, one skilled in the art will appreciate that the shim members 2611 can also be provided parallel or perpendicular to the interface of the first layer and the second layer.

Figure 55A:
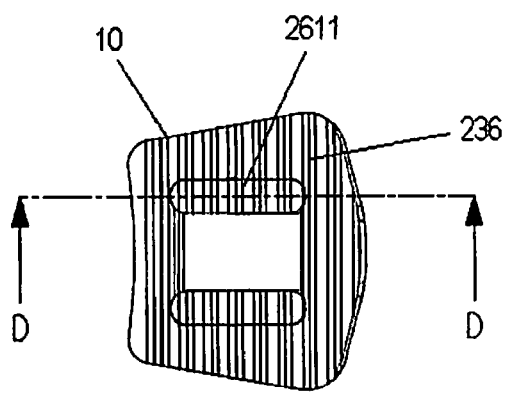
FIGS. 55A and 55B illustrate an alternative implant having shims according to some embodiments.
Figure 55B:
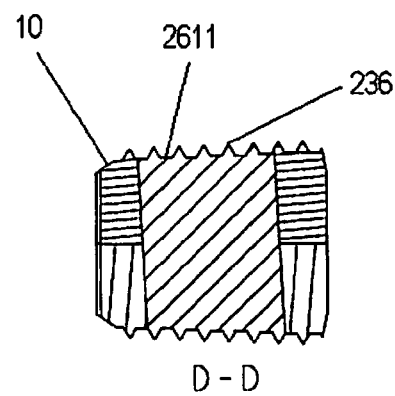

FIGS. 55A and 55B illustrate an alternative implant having shims according to some embodiments. The implant 10 is similar to the implant shown in FIG. 54A, but also includes a plurality of ridges 236 on superior and/or inferior surfaces thereof. The ridges 236 advantageously help to grip adjacent vertebral surfaces. As shown in the illustrated embodiments, the ridges 236 can formed on both the body of the spacer 10, as well as on the surfaces of the shim members 2611. In alternative embodiments, the body of the spacer 10 includes ridges, while the shim members 2611 do not include ridges. In some embodiments, as shown in FIG. 55B, the ridges 236 can be separated by a planar surface such that they are maintained a certain distance from one another. In other embodiments, as shown in FIG. 56B, the ridges 236 are not separated by a planar surface between one another. Rather, the ridges 236 are continuously formed and in general, do not extend from a planar surface. While the illustrated embodiments show surface texture comprised of ridges, other types of surface texturing can also be provided, including protrusions, teeth, and peg members.

Figure 56A:
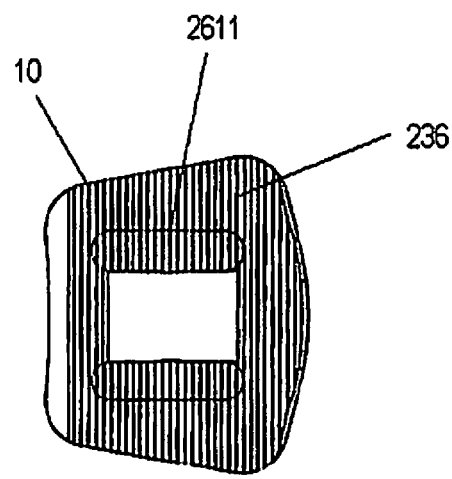
FIGS. 56A-56C illustrate an alternative implant having shims according to some embodiments.
Figure 56B:
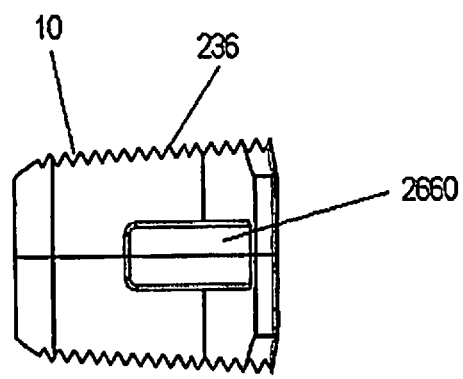
Figure 56C:
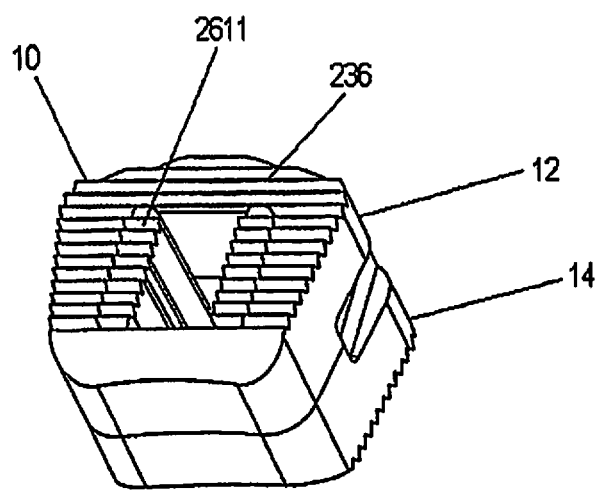

FIGS. 56A-56C illustrate an alternative implant having shims according to some embodiments. The implant 10 is similar to that shown in FIG. 55A, but includes ridges 236 that are not spaced from one another. The ridges 236 in FIG. 56A thus do not extend from a planar surface, but rather are continuously formed across the superior and/or inferior faces of the implant 10. In contrast to the ridges in FIG. 55A that extend from a substantially planar surface, in the embodiment in FIG. 56A, the ridges themselves comprise the superior and/or inferior surfaces. In other words, there is no clear planar or base surface from which the ridges extend. In some embodiments, the entire superior and/or inferior faces of the implant 10 are covered in ridges or some type of surface protrusion. In other embodiments, and as shown in the figures, the ridges 236 need not extend across the entire superior and/or inferior surfaces, thereby allowing for a ridge-free portion on the surfaces. In some embodiments, the ridge-free portions of the implant 10 can advantageously be grasped by an instrument, such as an insertion instrument, to facilitate insertion or can be used as a distraction end.

In addition, as shown in FIG. 56B, the implant 10 further includes one or more instrument gripping side channels 2660. In some embodiments, the one or more side channels 2660 comprise a recess having walls without additional openings therein. In other embodiments, the side channels 2660 comprise a recess having walls that include additional openings (e.g., scalloped openings) formed therein. Advantageously, an insertion instrument can be used to grip the one or more side channels, thereby helping to deliver the implant into a desired surgical space.

FIGS. 58A-58D illustrate an alternative implant for receiving a plug according to some embodiments. The implant 10 can have a concave face that opposes a convex face. In the center of the implant is an opening 2608 for receiving a plug 2610. As shown in FIG. 58B, the plug can have an upper flat surface and a bottom angled surface. As shown in FIG. 58D, the implant 10 can be lordotic in order to fit into a desired anatomical space.

Figure 59A:
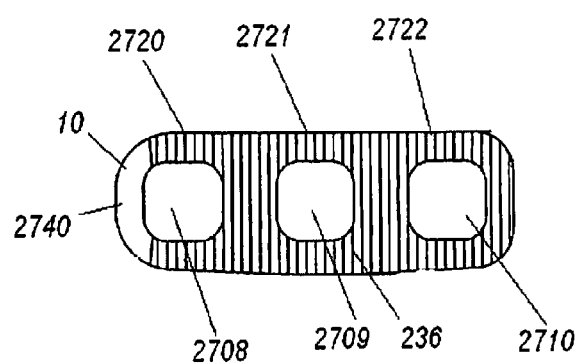
FIGS. 59A-59C illustrate an alternative implant assembled from two or more members in series according to some embodiments.
Figure 59B:
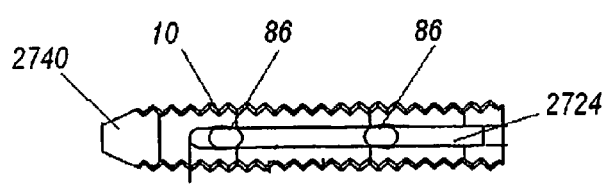
Figure 59C:
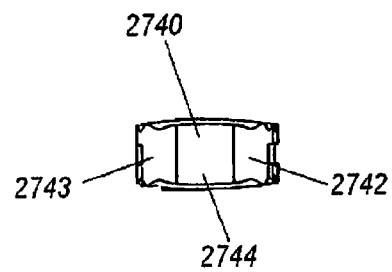

FIGS. 59A-59C illustrate an alternative implant assembled from two or more members in series according to some embodiments. The implant 10 can be assembled from two or more members of cortical bone in series and/or parallel. This advantageously helps to create an implant that is longer and/or wider than a single-piece, natural bone diameter would allow for. In some embodiments, the implant 10 in the present embodiment can be used in a lateral approach; however, one skilled in the art will appreciate that the implant can be used via other approaches as well. Advantageously, the designs described herein are strong enough to withstand a variety of loading situations placed on the implant from insertion, while providing variability for manufacturing.

As shown in FIG. 59A, the implant 10 can be formed of multiple members (e.g., cortical members) formed in series. In the present embodiment, the implant 10 includes three rings or members of cortical bone 2720, 2721, 2722 (e.g., from femoral rings) that are placed in series and attached to one another. Each of the members 2720, 2721, 2722 includes an upper surface and a lower surface having a plurality of ridges to assist in engage adjacent vertebral surfaces. The ridges advantageously prevent expulsion of the implant during increased loading on the implant 10.

In addition, each of the members 2720, 2721, 2722 advantageously includes its own respective hole or opening 2708, 2709, 2710 for receiving graft material therethrough. The openings 2708, 2709, 2710 can be square-shaped with rounded edges. In some embodiments, a bone plug (e.g., cortical or cancellous) can also be provided through the opening.

As shown in FIG. 59A, each of the member 2720, 2721, 2722 can have its own distinct shape and features. For example, member 2720 can have a curved, tapered leading end 2740 that can advantageously serve as a distraction edge in some embodiments. Member 2721, which is in the middle of the three members, assumes a different shape (e.g., square) with actual corners. Trailing member 2722 can have curved edges similar to leading member 2720. However, trailing member 2722 need not have a tapered edge.

To assemble the members 2720, 2721, 2722 in series and for parallel, fixation members or bone pins can be inserted through the members. As shown in FIG. 59B, the bone pins can be inserted through holes 86 that are formed through the bodies of the members 2720, 2721, 2722. In some embodiments, the bone pins extend across the interface of at least two of the members 2720, 2721, 2722 to fix the members together. In some embodiments, the bone pins are inserted at an angle or diagonally across the interface of at least two of the members 2720, 2721, 2722, while in other embodiments, the bone pins are inserted vertically. As shown in FIG. 59B, the bore holes 86 for receiving the bone pins can have openings that open within one or more slots 2724 formed on the side of the members 2720, 2721, 2722. In alternative embodiments, the members 2720, 2721, 2722 can be attached to one another via a different means, such as an adhesive. In addition, in some embodiments, the members 2720, 2721, 2722 may have complementary mating surfaces that interlock with one another, such as complementary "S" curves or step shapes as shown above. Any type of fastening mechanism, such as shims, biscuits, or interlocking "puzzle" features can be used instead of or in addition to the bone pins described above.

As shown in FIG. 59B, one or more of the members 2720, 2721, 2722 can have one or more slots 2724 formed on a sidewall thereof. For example, in some embodiments, an extended slot will traverse at least partially along the side of each of members 2720, 2721, 2722. In addition, a second slot (not shown) can be provided on an opposite side of the members. In some embodiments, a grasping or insertion instrument can be used to grab and hold the members to thereby deliver the adjoined members to a desired vertebral space.

FIG. 59C shows a front view of the tapered leading end 2740 of the implant 10. The tapered leading end 2740 can comprise a convex surface formed of a substantially flat surface 2742 with adjacent curved surfaces 2743, 2744. The adjacent curved surfaces 2743, 2744 transition into the sidewalls of the spacer along its longitudinal length.

Figure 60A:
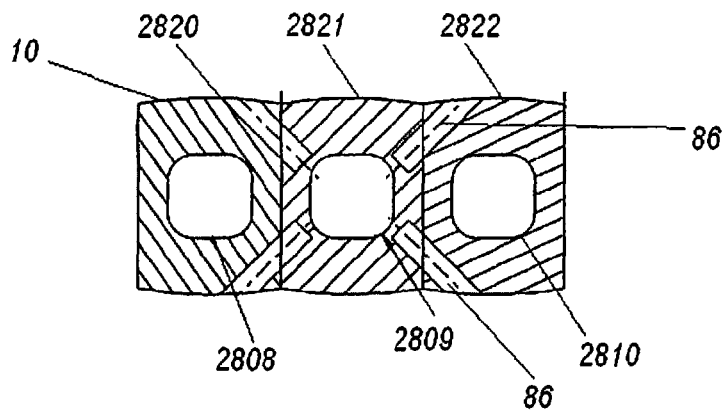
FIGS. 60A-60D illustrate an alternative implant assembled from two or more members in series according to some embodiments.

FIGS. 60A-60D illustrate an alternative implant assembled from two or more members in series according to some embodiments. In the present embodiment, the members 2820, 2821, 2822 comprise members made from cortical bone that are substantially of the same shape. Each of the members 2820, 2821, 2822 includes opposing convex walls separated by straight walls. Each member also includes respective graft openings 2808, 2809, 2810 for receiving graft material therein. As shown in FIG. 60A, each of the members 2820, 2821, 2822 includes at least one bore hole 86 extending therethrough. The bore hole 86 through one member is continuous with a bore hole through another member so as to allow a bone pin or fastener to be inserted across an interface between two members. In some embodiments, the bore holes 86 are diagonal, while in other embodiments, the bore holes are vertical or horizontal.

Figure 60B:
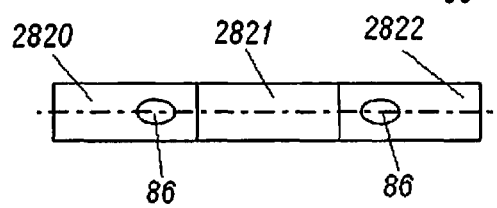

As shown in FIG. 60B, the bore holes 86 can be formed such that members 2820 and 2822 have openings through their convex faces. Middle member 2821 will not have bore holes 86 that extend through its convex faces.

Figure 60C:
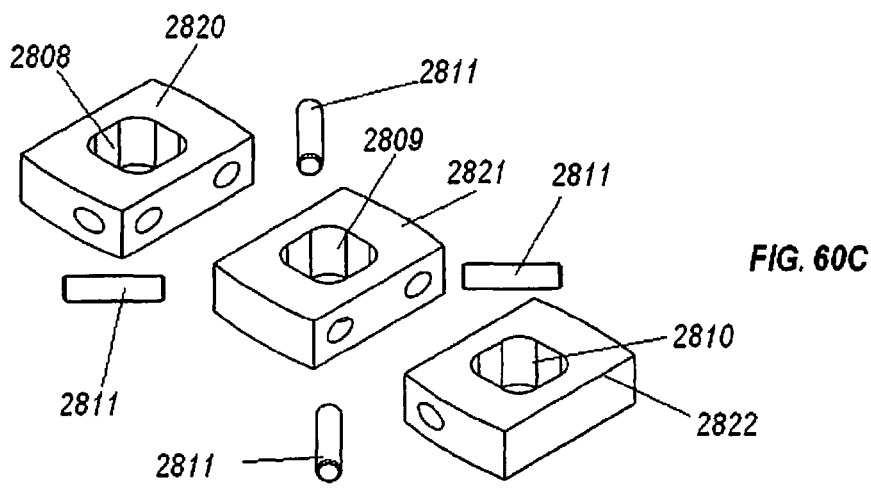
Figure 60D:
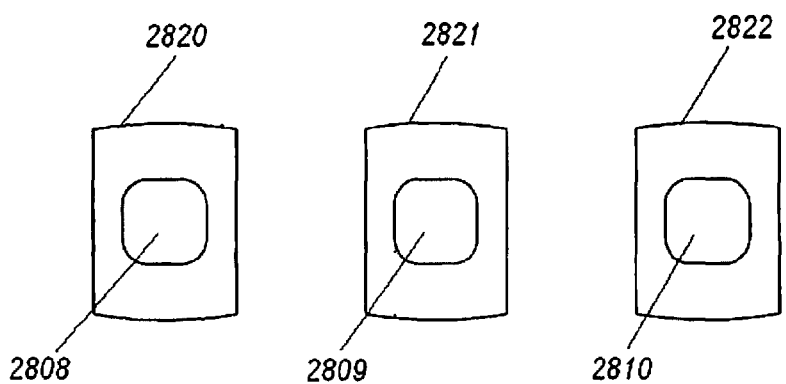

As shown in FIG. 60C, one or more bone pins 2811 can be inserted through the bore holes 86. Advantageously, each interface between members has at least two bone pins 2811. For example, the interface between member 2820 and 2821 has at least two bone pins, while the interface between member 2821 and 2822 has at least two bone pins. This advantageously forms a secure locking mechanism that secures the members together. Any of the other attachment mechanisms, such as adhesives or complementary mating features, can also be applied to the present embodiment.

The embodiments in FIGS. 59A-60D provide implants that are strong to withstand loading. In addition, the implants can be assembled in series, and provide desired variability to a surgeon. In some embodiments, the implants can be preassembled such that a surgeon can pick from a number of different configurations. In other embodiments, the surgeon can assemble the implants himself prior to performing a surgery. In some embodiments, the implants can comprise cortical bone (e.g., femoral rings) that are attached in series to allow the implant to span the majority of a disc space, thereby providing a larger area for fusion and greater stability. As the members are advantageously attached in series, the total length of the implant can be increased to cover more surface area in an intervertebral space. Cutouts or slots in the implant advantageously allow the surgeon to use an instrument designed with the implant to firmly hold and precisely place the implant in a desired intervertebral space.

Figure 61:
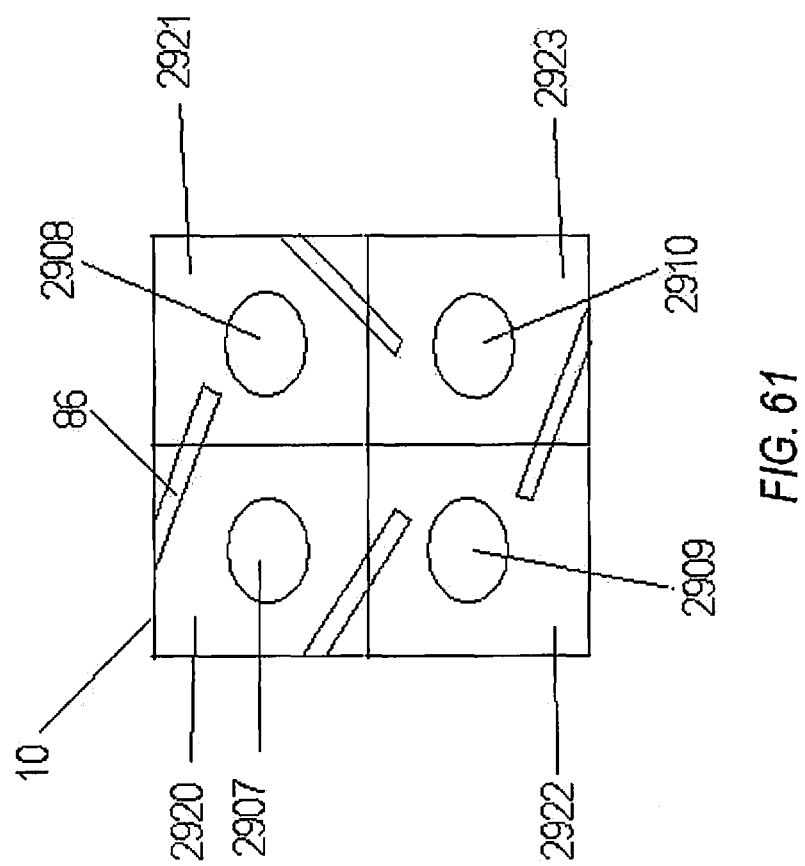
FIG. 61 illustrates an alternative implant assembled from two or more members in series and in a stacked configuration according to some embodiments.

FIG. 61 illustrates an alternative implant assembled from two or more members in series and in a stacked configuration according to some embodiments. In the present embodiment, four members 2920, 2921, 2922 and 2923 are arranged side-by-side. In some embodiments, the members are arranged in series (e.g., member 2920 is arranged side-by-side with member 2921). Alternatively, the members can be viewed as on the same plane but stacked. For example, members 2920 and 2921 are stacked on top of members 2922 and 2923. Each of the members includes its own graft hole 2907, 2908, 2909 and 2910. In addition, at least one bore hole 86 extends between the interfaces amongst each of the members.

For some implants formed of two or more members, it may be difficult to find enough purchase through the bone members for using the pinning methods described above. In addition, under certain circumstances, using pins as described above can allow undesired rotation of one member relative to another. In order to solve these issues, it has been found that using one or more compressive pins—particularly in the form of a "figure 8" shape—can help secure the two or more members together and reduce undesired rotation between the members. Advantageously, the use of the compressive pins described herein allows for a smaller amount of bone thickness for securing two members together since the pin can run parallel to assembled faces rather than perpendicular. This allows the compression pin to make contact with a larger surface area along the assembly places in a shorter distance and eliminates any potential axis of ration between assembled parts.

FIGS. 62A and 62B illustrate different views of an alternative implant with a figure 8 pin according to some embodiments. FIG. 62A shows the implant 10 assembled, while FIG. 62B shows the implant 10 unassembled. The implant 10 comprises a body 3000 formed of at least two sub-bodies or members 3021, 3022 formed of bone. Each of the members 3021, 3022 includes a hole or recess formed therein—member 3021 includes recess 3015A and member 3022 includes recess 3015B. When the two members 3021, 3022 are assembled with one another, the two holes 3015A and 3015B are placed in alignment and form an elongated hole or recess 3015. The recess 3015 is configured to receive a compression pin 3050 therein. In some embodiments, the compression pin 3050 comprises a press pin that is forced into the elongated recess 3015. Advantageously, the compression pin 3050 can comprise a butterfly or "figure 8" shape, whereby the pin 3050 includes two larger, oversized ends surrounding a narrower center section. By using such a pin 3050, the two or more bone members 3021, 3022 can advantageously be joined together with at least a partially compressive force, with minimal purchase depth and in a manner that prevents rotation of adjoining surfaces.

As shown in FIG. 62B, in some embodiments, the implant 10 can be comprised of two members 3021, 3022 that when adjoined have two holes 3015—one of the upper face of the implant 10 and one on the lower face of the implant 10. Each of the two holes 3015 can accommodate a compression pin 3050A, 3050B. With two separate compression pins, the multi-piece implant 10 can advantageously be secured on both the upper and lower surfaces.

As shown in FIGS. 62A and 62B, the implant 10 can also include one or more recesses 3013 for engagement with an insertion instrument. As shown in the illustrated embodiment, each of the implants 10 includes an engagement recess 3013 on opposite sides. In some embodiments, the engagement recesses 3013 can advantageously be positioned adjacent bump-out portions 3014. The bump-out portions 3014 advantageously allow the implant 10 to be secured to a plate, shown for example in FIG. 2A of U.S. Ser. No. 13/785,434 filed on Mar. 5, 2013 and herein incorporated by reference in its entirety, as the bump-out portions 3014 of the implant 10 can be inserted and maintained in the windows (identified in the '434 application by reference numeral 72) formed on the side arms of the plate.

FIG. 63 illustrates an unassembled implant with a figure 8 pin according to some embodiments. From this view, one can see that the implant 10 is comprised of three different components—a first bone member 3021, a second bone member 3022 and a compression pin 3050 in the form of a figure 8. In some embodiments, the compression pin 3050 is a matching fit with the recesses 3015A and 3015B, which adjoin to form an elongated recess 3015. In other words, the shape and size of the compression pin 3050 substantially or completely matches the shape and size of the elongated recess 3015. In other embodiments, the compression pin 3050 is of a different size and/or shape from the elongated recess 3015. For example, the compression pin 3050 can comprise two large rounded ends (as shown in FIG. 63), while the elongated recess 3015 can comprise edges (e.g., such as part of a rectangle).

FIGS. 64A and 64B illustrate different views of an assembled implant with a figure 8 pin according to some embodiments. From these views, one can see the location of the elongated hole 3015 for receiving the compression pin 3050 therein. As shown in the figures, the first bone member 3021 and the second bone member 3022 can have ridges or protrusions 3036 that extend on their superior and inferior surfaces, thereby helping to prevent expulsion of the assembled implant in between two vertebral bodies. In some embodiments, and as shown in FIG. 64B, the elongate hole 3015 for receiving the compression pin 3050 can be formed on a side face of the implant 10, such that it is not cut into the protrusions 3036 of the implant 10. While the embodiment herein shows a single compression pin 3050, in other embodiments, two or more compression pins 3050 can be provided to secure the implant 10. In some embodiments, the protrusions 3036, as well as an insertion chamfer on the body of the implant, can be formed after assembling the two members 3021, 3022 together with a compression pin 3050. In other embodiments, the protrusions 3036 and/or insertion chamfer are formed before assembling the two members 3021, 3022 together with a compression pin 3050.

Figure 65B:
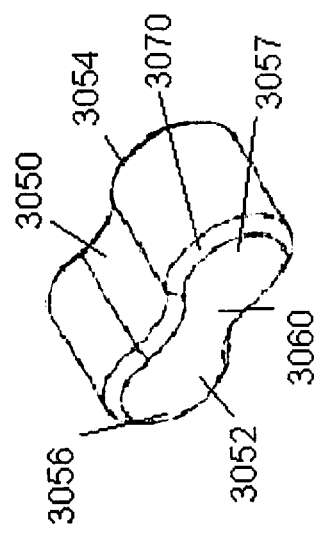
FIGS. 65A and 65B illustrate different views of a figure 8 pin according to some embodiments.
Figure 65A:
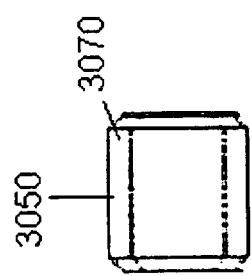

FIGS. 65A and 65B illustrate different views of a figure 8 pin according to some embodiments. As shown in the figures, the compression pin 3050 is in the shape of a butterfly or figure 8 having a first large rounded section 3056, a second large rounded section 3057 and a narrower mid-section 3060. The compression pin 3050 includes a superior surface 3052 and an inferior surface 3054. While in the illustrated embodiment, the superior surface 3052 and the inferior surface 3054 do not have surface ridges or protrusions, in other embodiments, the superior surface 3052 and inferior surface 3054 do have surface ridges or protrusions. In addition, as shown in FIGS. 65A and 65B, the compression pin 3050 can have a cut-out or chamfered portion 3070 that extends around the perimeter of the compression pin 3050. Such a cut-out or chamfered portion 3070 advantageously rounds the edges of the compression pin 3050, thereby making the implant easier to insert into a disc space from any side of the implant. While the compression pin 3050 is illustrated as having rounded edges in the illustrated embodiments, in other embodiments, the compression pin 3050 can have enlarged edges or other shapes, including octagonal, square, or rectangular. In some embodiments, the compression pin 3050 can be in the shape of an i-beam. In addition, the compression pin 3050 need not be symmetrical. For example, enlarged section 3056 can be larger or shaped differently from enlarged section 3057.

Figure 66B:
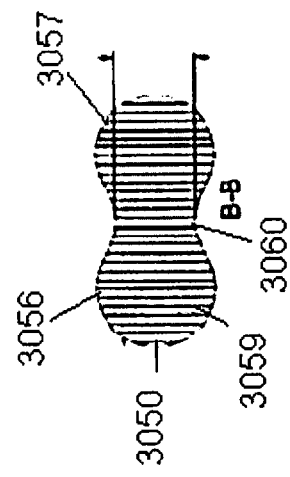
FIGS. 66A and 66B illustrate different views of an alternative figure 8 pin according to some embodiments.
Figure 66A:
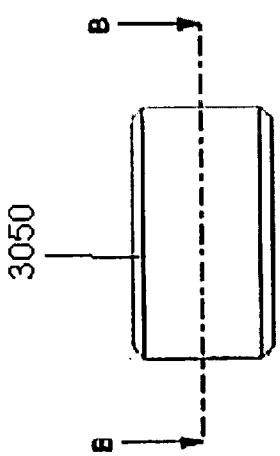

FIGS. 66A and 66B illustrate different views of an alternative figure 8 pin according to some embodiments. The compression pin 3050 is of a similar shape to the pin shown in FIGS. 65A and 65B and shares many similar features, including a first large rounded section 3056, a second large rounded section 3057 and a narrower mid-section 3060. In contrast to the pin in FIGS. 65A and 65B, the pin 3050 comprises surface ridges or protrusions 3059 that extend along superior and/or inferior surfaces of the pin 3050. Accordingly, the pin in FIGS. 66A and 66B can be used on a superior surface and/or inferior surface of an implant that has protrusions, while the pin in FIGS. 65A and 65B can be used on a side surface in between superior and inferior surfaces of an implant, if desired.

Additional Characteristics

In addition to those features discussed above, additional features are now described. Any combination of features are possible to include in the implants discussed above.

In some embodiments, the implants can be formed of allograft, xenograft, synthetic material or combinations thereof. Specific materials possible for use include cortical bone, cancellous bone, cortico-cancellous bone, collagen, PEEK, titanium, stainless steel, PLA, PLDL and other materials.

In some embodiments, the implants are formed monolithically. In other embodiments, the implants are multi-piece, and are composed of two or more layers. The layers can be generally planar; however, in some embodiments, the multi-piece implant can include non-planar components. For example, an implant can comprise a first portion comprised of a square block member with a square hole formed therein and a second portion that is capable of filling in the hole.

The implants can be incorporated in multiple levels of the spine. For example, the implants described above can be suited for use in the cervical, thoracic and lumbar regions of the spine.

In some embodiments, the implants have substantially planar superior and inferior surfaces that are parallel and are not lordotic. In some embodiments, these implants can have anterior and posterior sides of similar height. In other embodiments, the implants have a degree of lordosis, such as up to 20 degrees with respect to a midplane. In some embodiments, these lordotic implants can have curved edges and/or curved upper/lower sides.

The implants described above can include a mid-plane that extends a length between a superior surface and an inferior surface. In some embodiments, the superior surface and inferior surface are parallel to the mid-plane. In other embodiments, only one of the superior surface and inferior surface are parallel to the mid-plane. And in another embodiment, neither the superior surface nor the inferior surface are parallel to the mid-plane.

The implants discussed above can have anterior, posterior and sidewalls of various shapes. For example, the walls can be curved, planar and angled.

For multi-layered implants composed of two or more layers, various interfaces can be formed between the implants. For example, the implant can include a mating face interface that is flat, curved, slanted, waffle-patterned, dovetail-patterned, t-shaped, lego, textured, or any other shape.

In some embodiments, the superior and/or inferior faces can include roughened surfaces. The roughened surfaces can include teeth, ribs, ridges, or any other types of surface protrusion. Among the surfaces that can include three-sided teeth, four-sided teeth, five-sided teeth, six-sided teeth and more, ridges, conical protrusions, saw teeth, pyramidal teeth and simple textures. In some embodiments, the tip of the surface protrusions can be rounded, sharp, flat, blunt or concave.

The implants can include a number of different insertion features. Among the insertion features include parallel slots, converging slots, dimples, channels, nubs, holes (threaded) and holes (non-threaded). These insertion features can be located in one or more places of the implant body, including into the body of the implant, along side walls, or on superior and inferior surfaces.

In some embodiments, the implants can include one or more graft holes. The graft holes can be of various shapes, including circular, triangular, square, oval tear-drop, tapered, trapezoidal and rectangular. In some embodiments, the graft holes have a length that is greater than the width of adjacent walls, while in other embodiments, the graft holes have a length that is less than the width of adjacent walls. The graft holes can be placed in a number of positions, such as centrally, offset in an anterior-posterior direction, offset in a medial-lateral direction, or offset diagonally. In some embodiments, the graft hole can be formed of two or more holes that are aligned, while in other embodiments, the graft hole can be formed of two or more holes that overlap but may be axially offset from one another.

While the invention herein disclosed has been described by means of specific embodiments and applications thereof, numerous modifications and variations can be made thereto by those skilled in the art without departing from the scope of the invention.

What is claimed is:

1. An intervertebral implant for implantation in an intervertebral space comprising:
    a first bone member comprising a first superior surface, a first inferior surface, and a first opening formed in the first superior surface;
    a second bone member comprising a second superior surface, a second inferior surface, and a second opening formed in the second superior surface, wherein the first opening is configured to align side-by-side with the second opening to form an elongate opening along an upper surface of the implant when the first bone member is placed adjacent the second bone member; and
    a bone pin positioned in the elongate opening configured to securely lock the first bone member to the second bone member, wherein the bone pin comprises a first rounded section with a first width and a second rounded section with a second width and a midsection having width that is less than the first width and the second width, wherein the first rounded section is received in the first opening in the first bone member and the second rounded section is received in the second opening in the second bone member.

2. The implant of claim 1, wherein the first bone member comprises one or more protrusions on each of the first superior surface and first inferior surface, and the second bone member comprises one or more protrusions on each of the second superior surface and the second inferior surface.

3. The implant of claim 1, wherein the bone pin comprises one or more protrusions on a surface of the bone pin.

4. The implant of claim 1, wherein the bone pin comprises a figure 8 pin wherein the first rounded section is substantially the same size as the second rounded section.

5. The implant of claim 1, wherein the bone pin comprises a figure 8 pin wherein the first rounded section is of a different size from the second rounded section.

6. An intervertebral implant for implantation in an intervertebral space comprising:
    a first bone member comprising a first opening;
    a second bone member comprising a second opening, wherein when the first bone member is positioned adjacent the second bone member, the implant includes a superior surface, an inferior surface, and an elongate opening formed by aligning the first opening side-by-side with the second opening along an upper surface of the implant; and
    a bone pin positioned in the elongate opening configured to securely lock the first bone member to the second bone member, wherein the bone pin comprises a first section with a first width and a second section with a second width and a midsection having width that is less than the first width and the second width, wherein the first section is received in the first opening in the first bone member and the second section is received in the second opening in the second bone member.

7. The implant of claim 6, wherein the first section and second section of the bone pin comprises rounded ends.

8. The implant of claim 6, wherein the first section and second section of the bone pin comprises squared ends.

9. The implant of claim 6, wherein the shape of the elongate opening is different from the shape of the bone pin received in the elongate opening.

10. The implant of claim 6, wherein the shape of the elongate opening is substantially similar to the shape of the bone pin received in the elongate opening.

11. The implant of claim 6, wherein the bone pin comprises protrusions on at least one surface.

12. The implant of claim 6, wherein the bone pin comprises a chamfer that extends around the periphery of the bone pin.

13. The implant of claim 6, wherein the first bone member and the second bone member are chamfered.

14. An intervertebral implant for implantation in an intervertebral space comprising:

a first bone member comprising a first opening;

a second bone member comprising a second opening, wherein when the first bone member is positioned adjacent the second bone member, the implant includes a superior surface, an inferior surface, and an elongate opening formed by aligning the first opening side-by-side with and the second opening along an upper surface of the implant; and a bone pin positioned in the elongate opening configured to securely lock the first bone member to the second bone member, wherein the bone pin comprises a compression pin having a chamfer that extends around its entire periphery.

15. The implant of claim 14, wherein the bone pin further comprises a first rounded end and a second rounded end.

16. The implant of claim 15, wherein the first rounded end and the second rounded end are on opposite sides of a thinner mid-section.

17. The implant of claim 14, wherein the superior surface includes ridges.

18. The implant of claim 14, wherein the bone pin comprises a FIG. 8 shaped pin.

\* \* \* \* \*